(12) United States Patent
Overes et al.

(10) Patent No.: US 8,784,419 B2
(45) Date of Patent: Jul. 22, 2014

(54) ADAPTABLE BONE FIXATION PLATE

(75) Inventors: Tom Overes, Langendorf (CH); Robert Frigg, Langendorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 673 days.

(21) Appl. No.: 12/766,228

(22) Filed: Apr. 23, 2010

(65) Prior Publication Data
US 2010/0274248 A1 Oct. 28, 2010

Related U.S. Application Data

(60) Provisional application No. 61/172,058, filed on Apr. 23, 2009.

(51) Int. Cl.
*A61B 17/80* (2006.01)

(52) U.S. Cl.
USPC .............................................. 606/71

(58) Field of Classification Search
USPC .................................. 606/280–284
See application file for complete search history.

(56) References Cited

U.S. PATENT DOCUMENTS

| 5,672,177 | A | | 9/1997 | Seldin |
| 6,129,728 | A | * | 10/2000 | Schumacher et al. .......... 606/71 |
| 2002/0183757 | A1 | * | 12/2002 | Michelson ....................... 606/71 |
| 2007/0213729 | A1 | | 9/2007 | Lindemann et al. |
| 2008/0147125 | A1 | * | 6/2008 | Colleran et al. ............... 606/280 |
| 2010/0082029 | A1 | * | 4/2010 | Ibrahim et al. .................. 606/71 |
| 2010/0145397 | A1 | | 6/2010 | Overes et al. |

FOREIGN PATENT DOCUMENTS

| WO | WO 2007/126622 | | 11/2007 | |
| WO | WO-2007/126622 A2 | * | 11/2007 | ............. A61B 17/56 |
| WO | WO 2010/124160 | | 10/2010 | |

OTHER PUBLICATIONS

International Patent Application No. PCT/US2010/032167: International Search Report dated Jul. 14, 2010, 7 pages.

* cited by examiner

*Primary Examiner* — Matthew Lawson
*Assistant Examiner* — Zade Coley
(74) *Attorney, Agent, or Firm* — Baker & Hostetler LLP

(57) ABSTRACT

An adaptable bone fixation plate and bone fixation system are configured to provide an anterior spinal plate with anterior pedicle screws includes a first plate section adjustably coupled to a second plate section using an arrangement that provides both superior-inferior adjustability of the plate sections as well as lateral adjustability of the plate sections to orient the first and second plate sections with respect to the desired orientation and disposition of two or more bone screws.

31 Claims, 19 Drawing Sheets

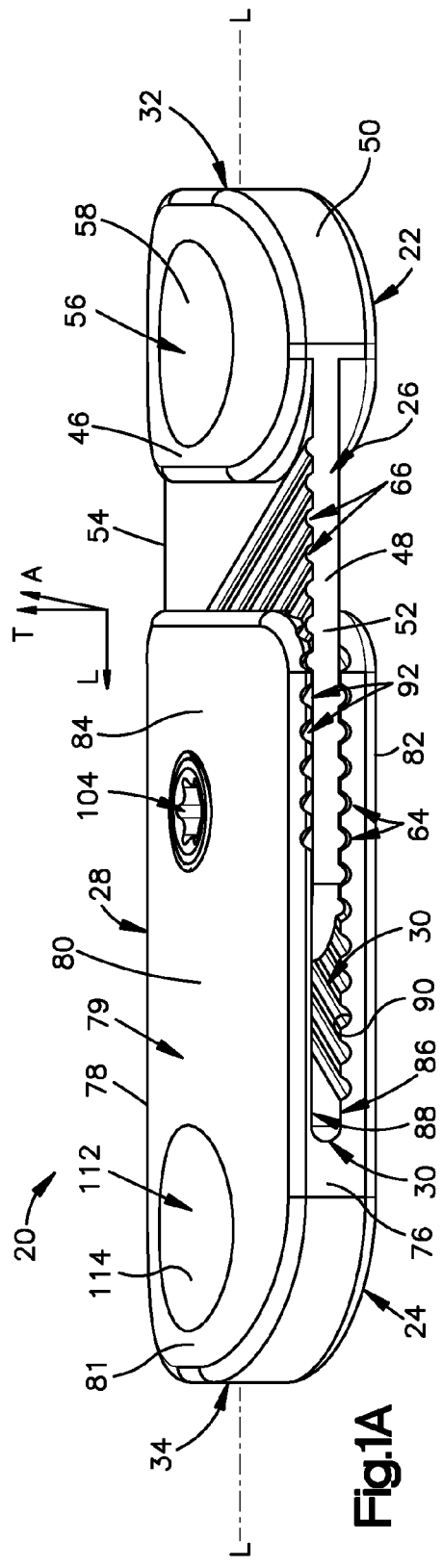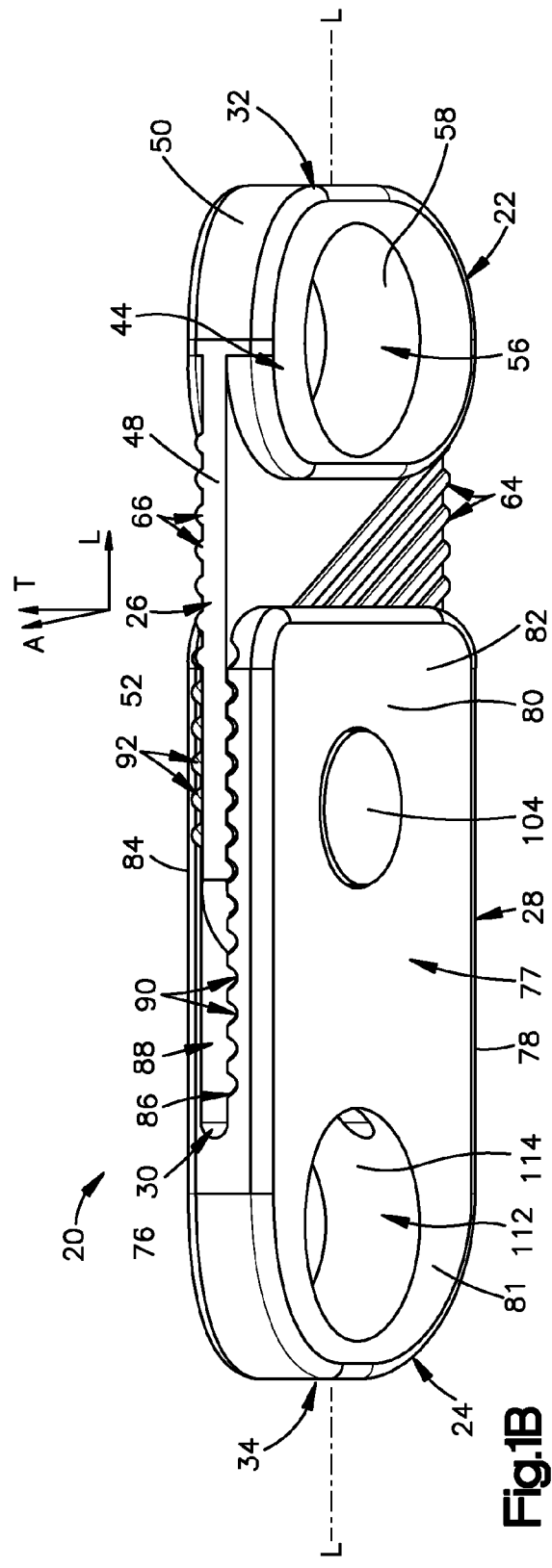
Fig.1A
Fig.1B

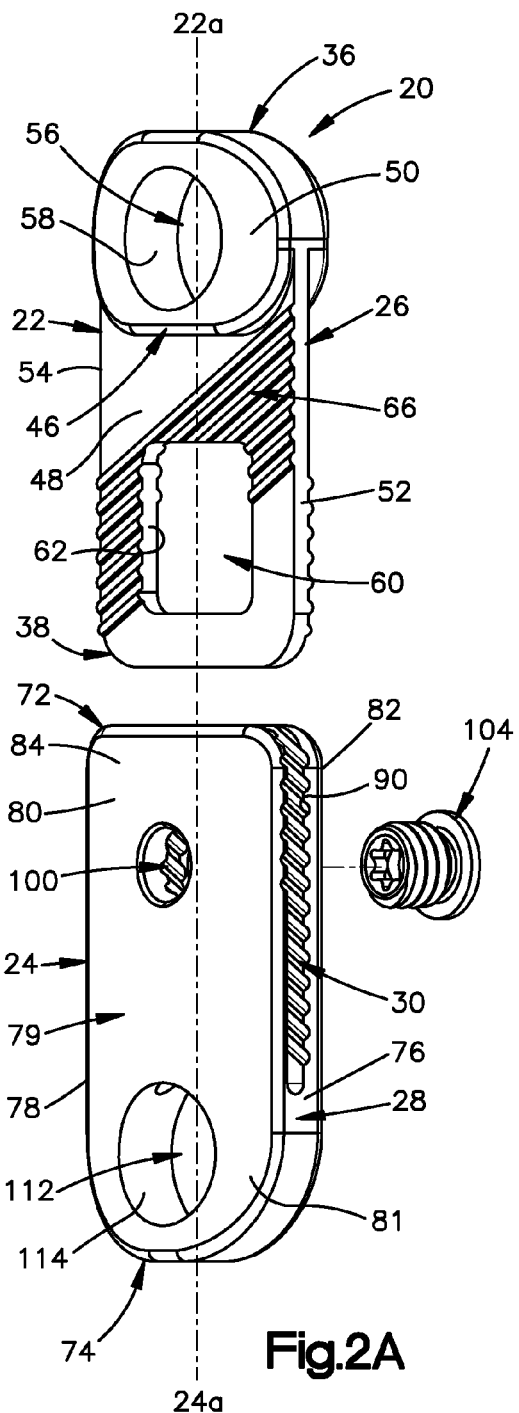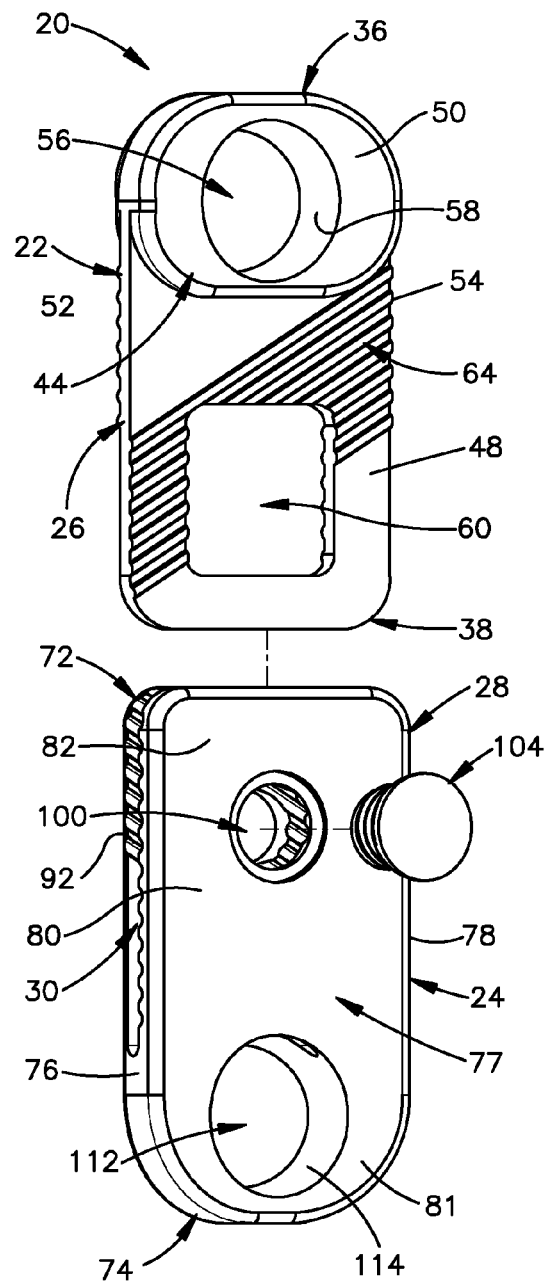

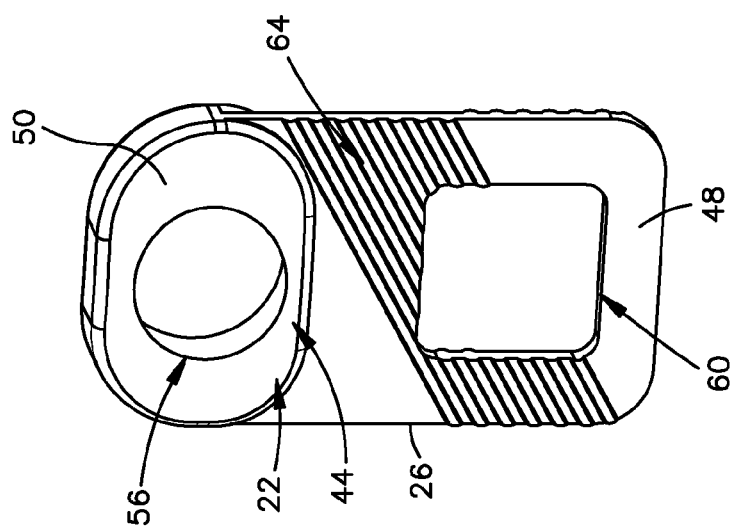
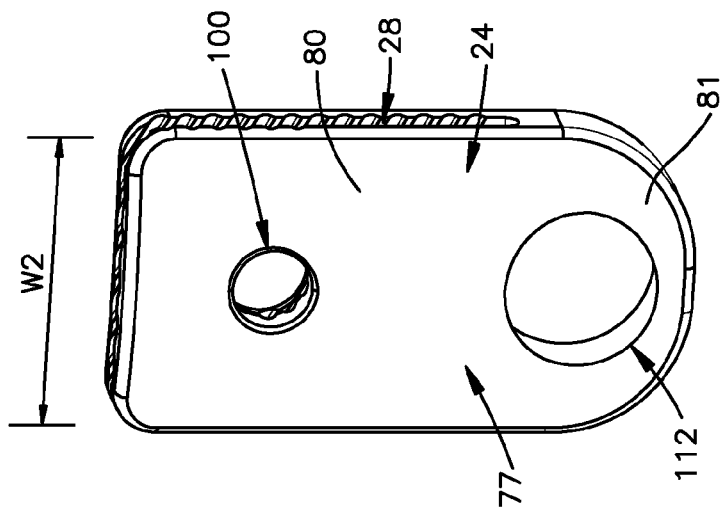
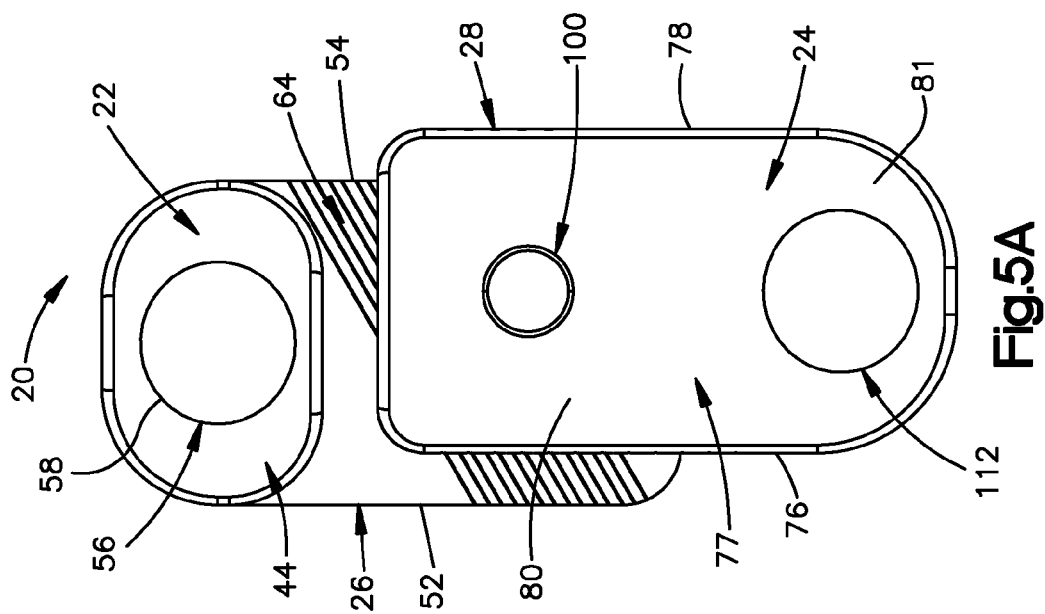

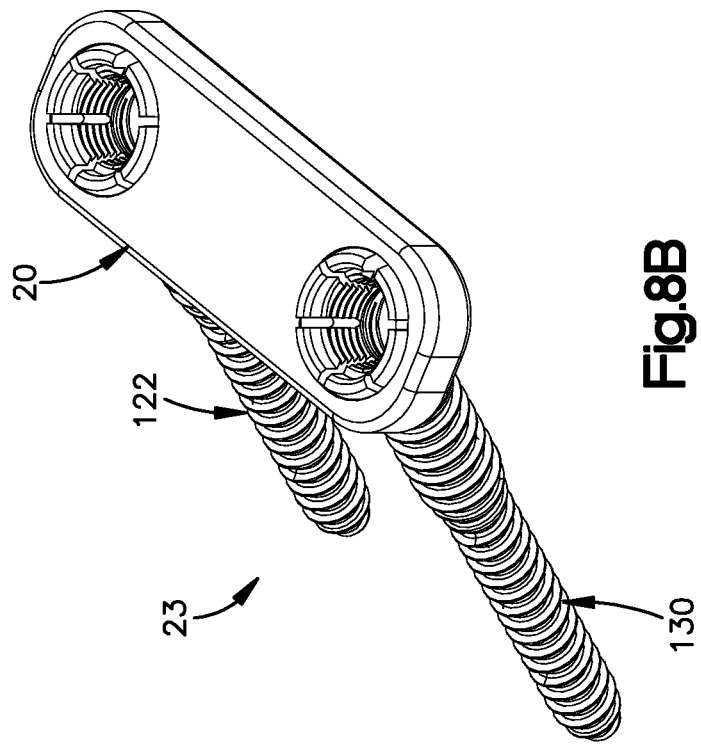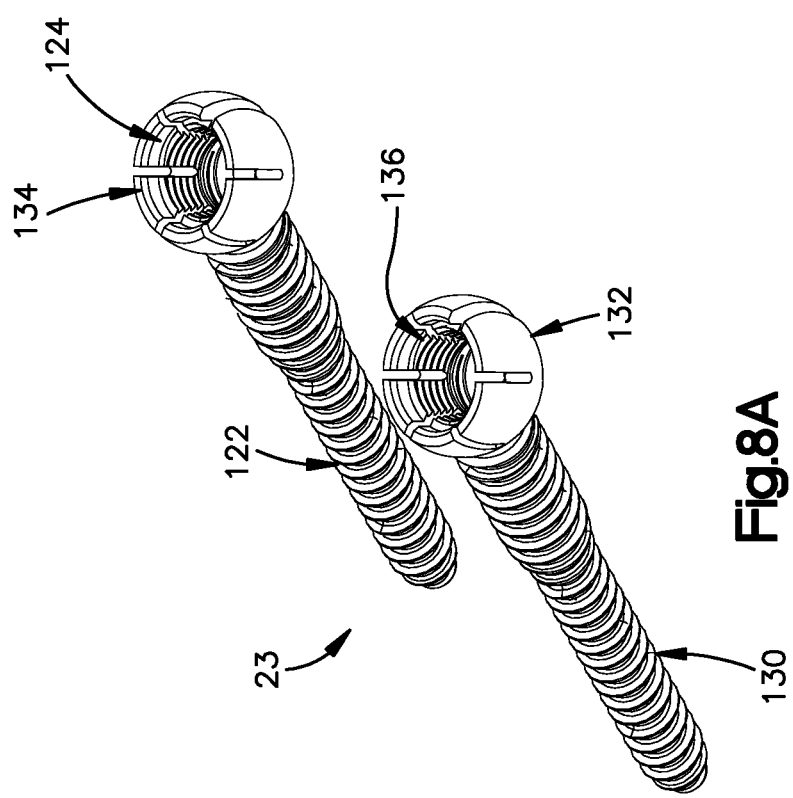

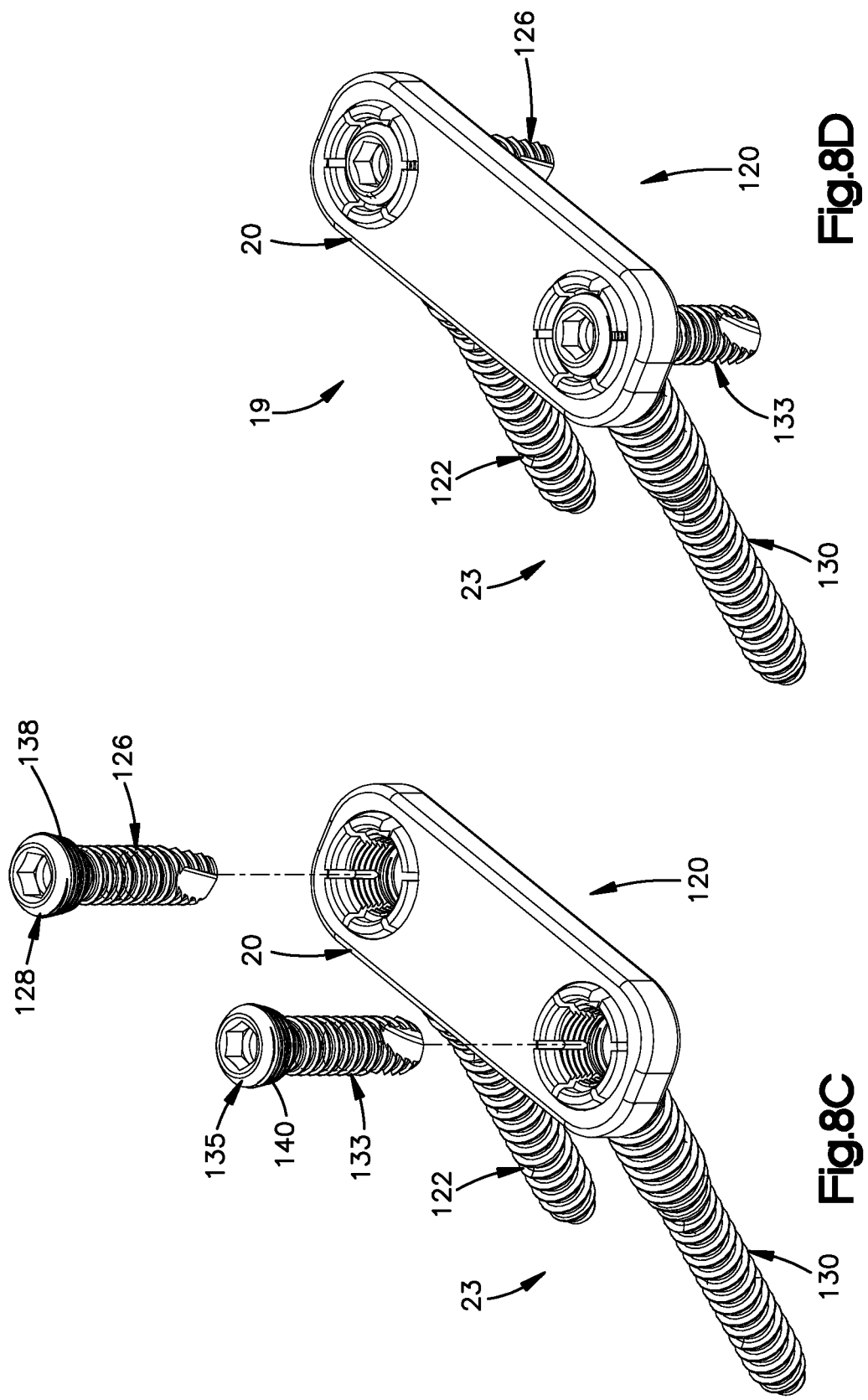

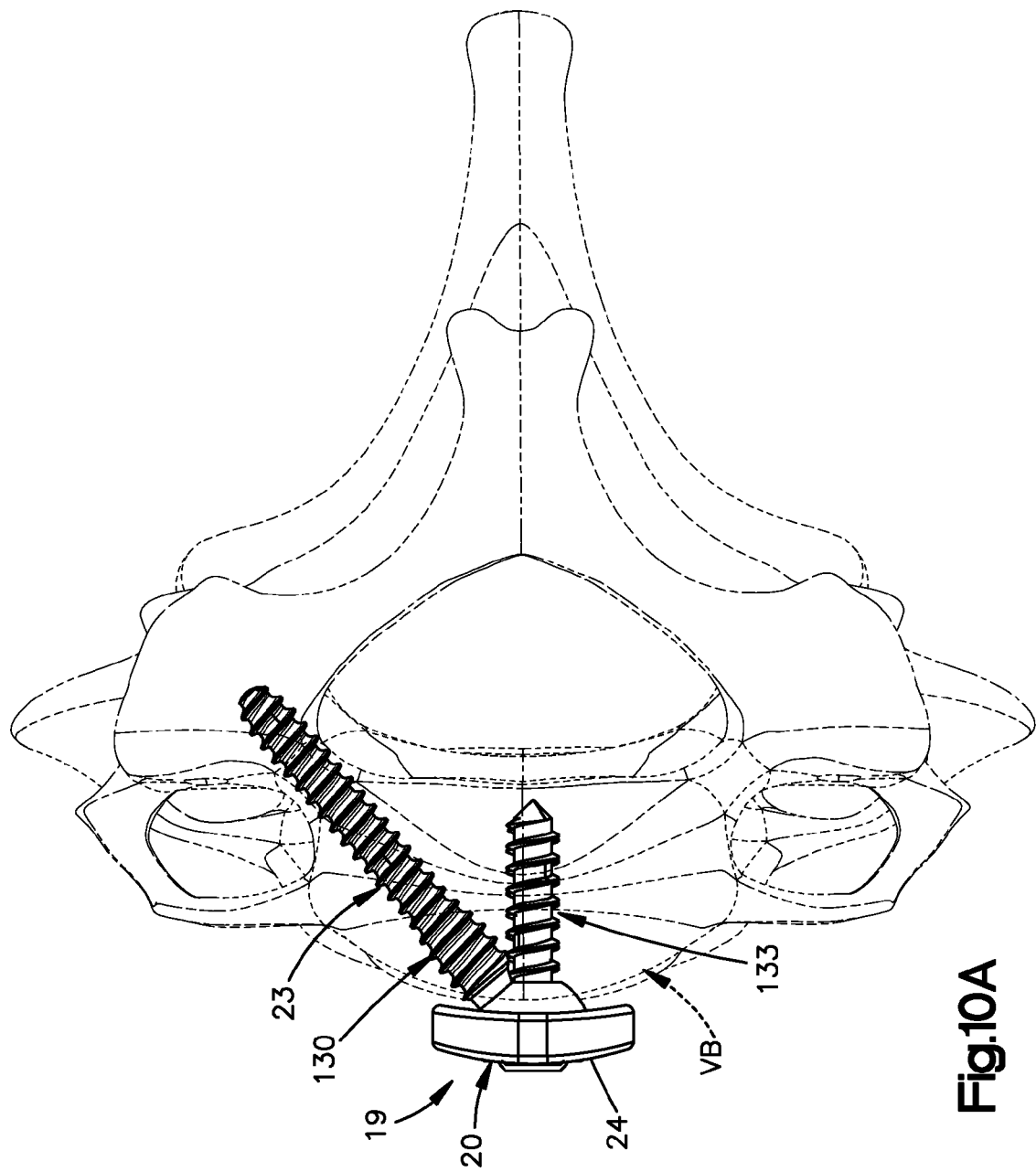

US 8,784,419 B2

ADAPTABLE BONE FIXATION PLATE

CROSS-REFERENCE TO RELATED APPLICATIONS

This claims priority to U.S. Provisional Patent Application Ser. No. 61/172,058 filed Apr. 23, 2009, the disclosure of which is hereby incorporated by reference as if set forth in its entirety herein.

BACKGROUND

Conventional bone fixation systems include bone plates that are implanted and affixed to bone via bone fasteners, which can include screws, nails, pins, and the like. For instance, a bone plate can be attached to opposite sides of a fractured long bone to promote fusion between the fractured bone segments. Bone plates can also be used for anterior transpedicular fixation systems for spinal correction. For instance, a conventional transpedicular fixation system can include an anterior spinal plate positioned along the anterior aspects of two or more vertebral bodies. Two or more anchoring screws can be driven into the vertebral bodies through corresponding screw holes in the plate, such that the screws terminate within the vertebral bodies.

SUMMARY

In accordance with one embodiment, a bone fixation system is configured to be fixed to at least one underlying bone. The bone fixation system includes a first plate section that defines a first body. The first body extends along a central axis between a superior end and an inferior end. The first body defines opposed inner and outer surfaces and a screw hole extending through the inner and outer surfaces. The first body includes at least one first rib extending from one of the inner and outer surfaces. The bone fixation system further includes a second plate section defining a second body that extends along a central axis between a superior end and an inferior end. The second body defines a channel configured to receive a portion of the first body such that the first body is initially translatable within the channel. The channel is defined by opposed interior surfaces, and wherein the second body defines at least one groove extending into at least one of the interior surfaces. The at least one groove is configured to mate with the at least one rib. The bone fixation system further includes a fastener configured to lock the rib in the groove so as to so as to prevent the first plate section from translating relative to the second plate section.

BRIEF DESCRIPTION OF THE SEVERAL VIEWS OF THE DRAWINGS

The foregoing summary, as well as the following detailed description of example embodiments of the adaptable plate and related constructs of the present application, will be better understood when read in conjunction with the appended drawings. For the purposes of illustrating the adaptable plate of the present application, there is shown in the drawings example embodiments. It should be understood, however, that the application is not limited to the precise arrangements and instrumentalities shown. In the drawings:

FIG. 1A is a top perspective view of an adaptable fixation plate constructed with one embodiment, having first and second plate segments;

FIG. 1B is a bottom perspective view of the adaptable plate illustrated in FIG. 1A;

FIG. 2A is an exploded top perspective view of the adaptable fixation plate illustrated in FIG. 1A;

FIG. 2B is an exploded bottom perspective view of the adaptable bone fixation plate illustrated in FIG. 1B;

FIG. 5A is a bottom plan view of the adaptable fixation plate as illustrated in FIG. 4B;

FIG. 5B is a bottom plan view of the second plate section as illustrated in FIG. 4C;

FIG. 5C is a bottom plan view of the first plate section as illustrated in FIG. 4D;

FIGS. 8A-D illustrate in side perspective views a method for mounting anchor-in-anchor or screw-in-screw bone fixation system to the adaptable plate illustrated in FIG. 1A-B, which is schematically illustrated in FIGS. 8A-D;

FIG. 10A is an end elevation view of the bone fixation system illustrated in FIG. 7A, secured to an anterior aspect of a vertebra, showing a generally translucent view of the patient's spine for clarity;

DETAILED DESCRIPTION

Figure 7A:
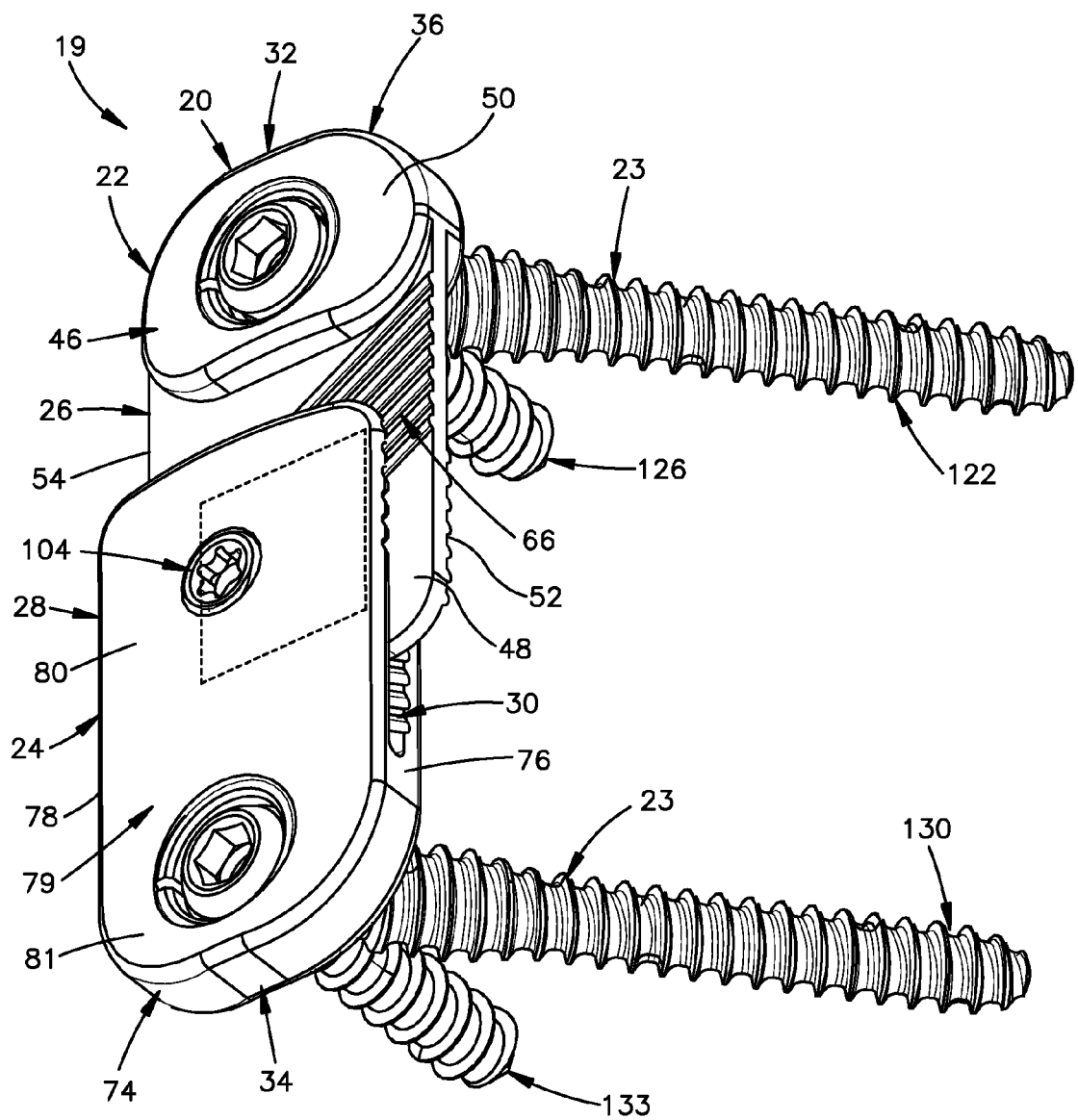
FIG. 7A is a perspective view of a bone fixation system including the adaptable fixation plate illustrated in FIGS. 1A-B and bone anchors or screws mounted to the plate.
Figure 7B:
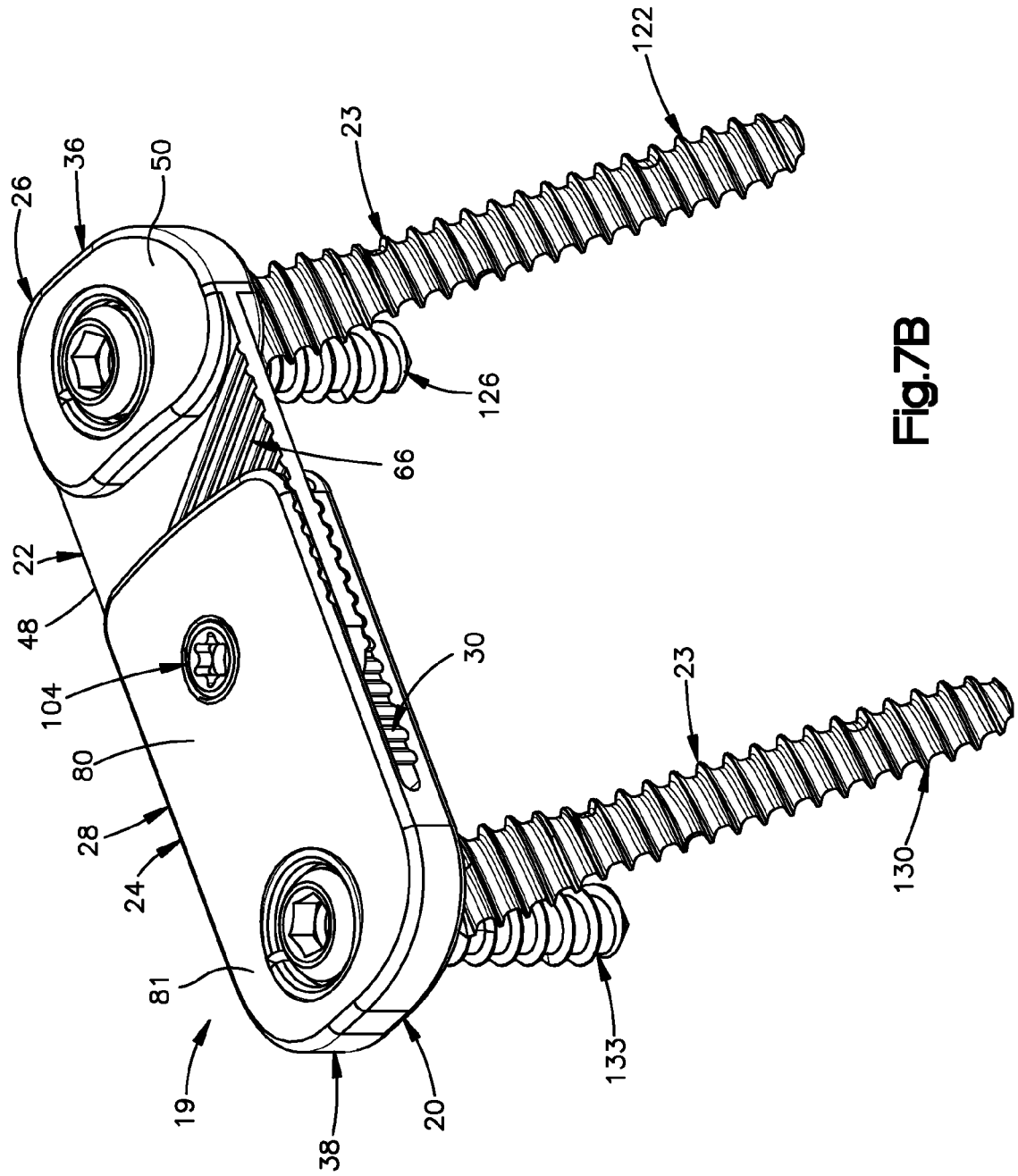
FIG. 7B is another perspective view of the fixation system illustrated in FIG. 7A.
Figure 10B:
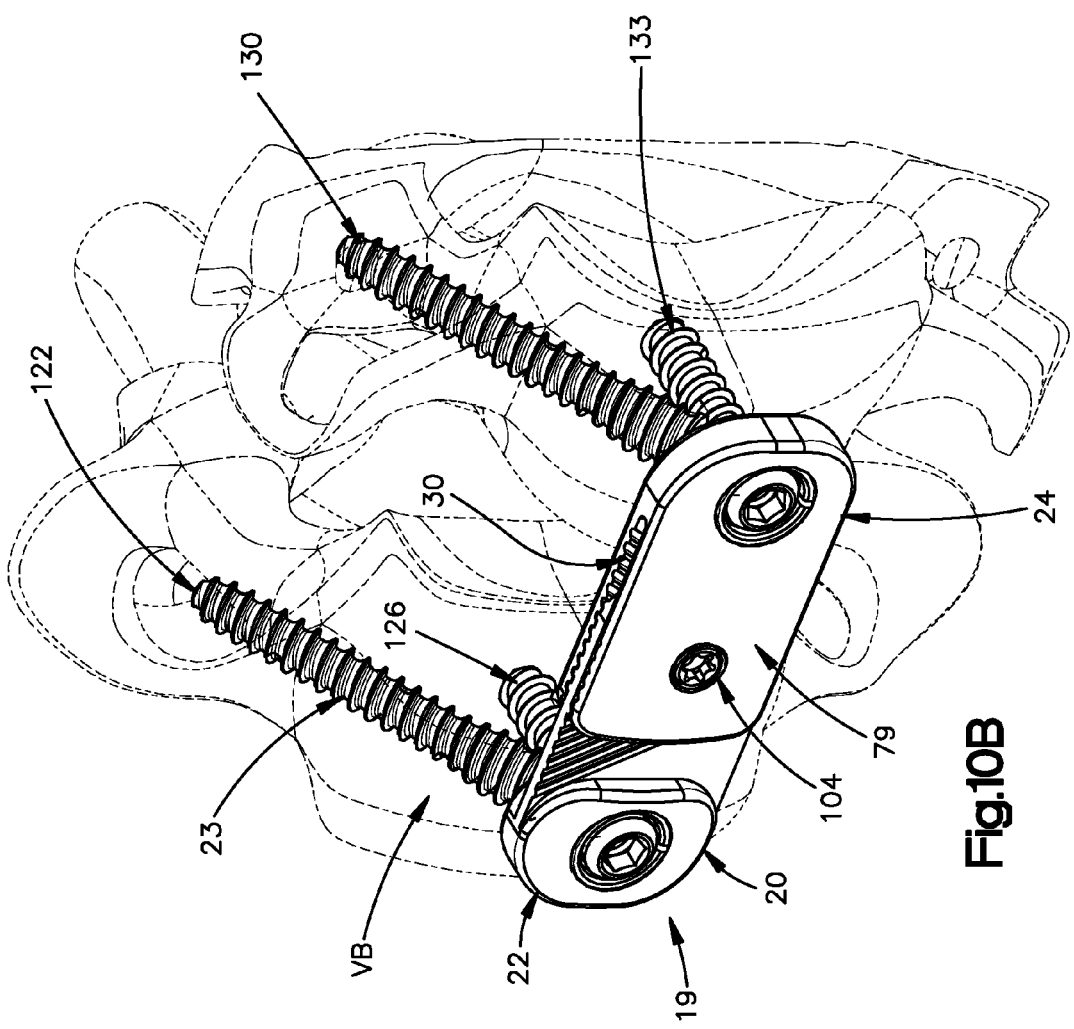
FIG. 10B is a perspective view of the bone fixation system illustrated in FIG. 10A.
Figure 10C:
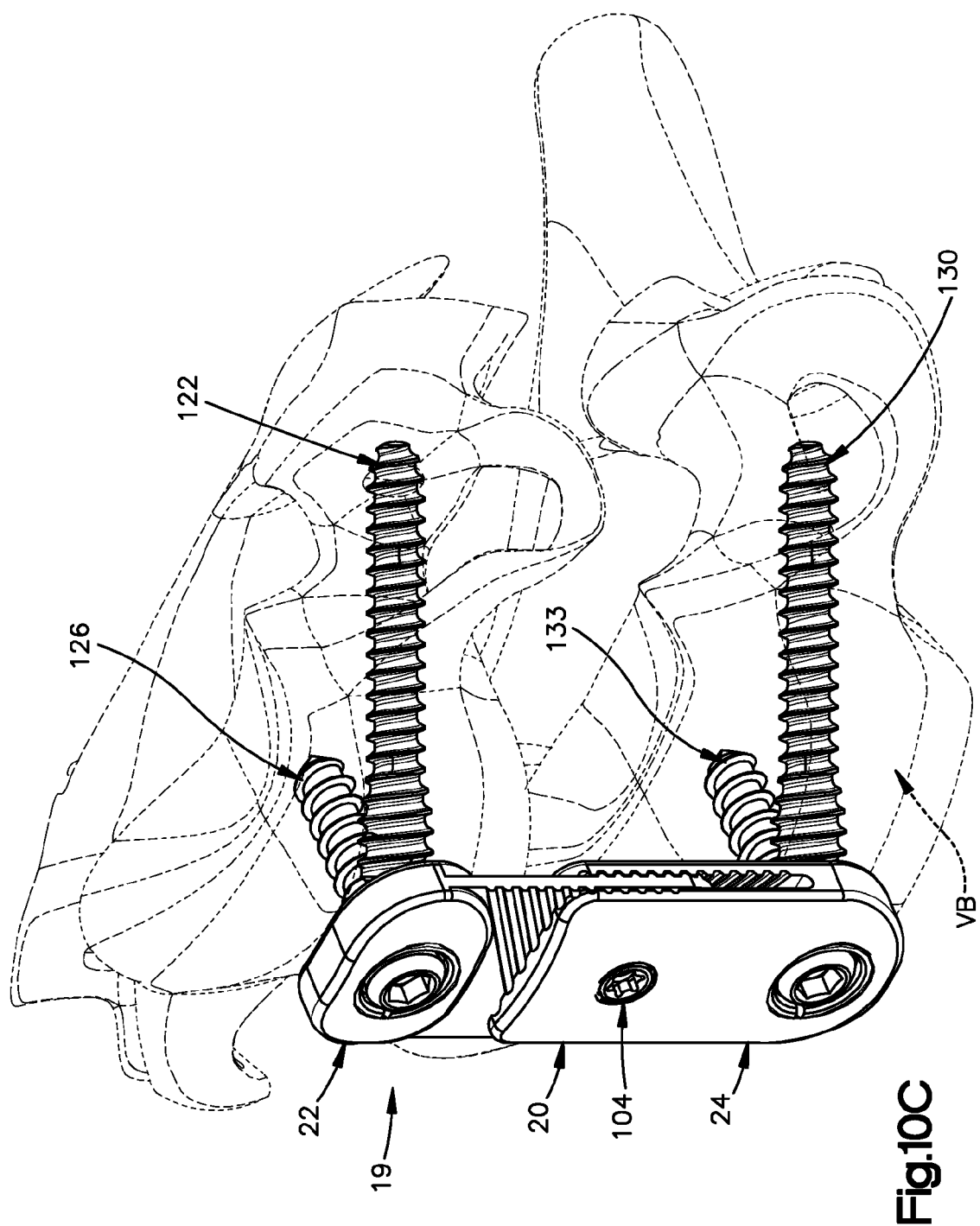
FIG. 10C is another perspective view of the bone fixation system illustrated in FIG. 10A.

Certain terminology may be used in the following description for convenience only and should not be considered as limiting in any way. For instance, a bone fixation system 19 includes an adaptable bone fixation plate 20 and one or more bone anchors 23, as illustrated in FIG. 7A. As shown in FIG. 10C, the bone plate 20 can extend vertically during use along a longitudinal direction L, and generally horizontally along a lateral direction A that is substantially perpendicular to the longitudinal direction L, and horizontally along a transverse direction T that is substantially perpendicular to both the longitudinal direction L and the lateral direction A. Thus, the bone plate 20 defines a length along the longitudinal direction L, a width along the lateral direction A, and a thickness along the transverse direction T. The bone plate 20 defines an upper or superior end 32 and an opposed lower or inferior end 34, such that the directional terms "upper" and "lower" and derivatives thereof refer to a direction from the lower end 34 towards the upper end 32, and from the upper end 32 towards the lower end 34, respectively.

The words "inward," "outward," "upper," "lower," "distal," and "proximal," refer to directions toward or away from, respectively, the geometric center of the bone fixation system 19 and its components. The words, "anterior", "posterior", "superior," "inferior" and related words and/or phrases designate positions and orientations in the human body to which reference is made and are not meant to be limiting. The terminology includes the above-listed words, derivatives thereof and words of similar import.

It should be appreciated that the directional terms are used herein with reference to the orientation of the bone fixation system 19 and its components as illustrated in FIG. 10C, and that the actual orientation of the bone fixation system 19 and its components may change during use. For instance, the longitudinal direction L is illustrated as extending along a vertical direction, and the lateral direction A and transverse direction T are illustrated as extending along a horizontal direction, however the directions that encompass the various directions may differ during use, depending, for instance, on the desired orientation of the bone fixation system 19 during use. Accordingly, the directional terms are used herein merely for the purposes of clarity and convenience only, in a non-limiting manner.

Referring to FIGS. 1A-B, the adaptable bone fixation plate 20 includes a first plate section 22 and a second plate section 24 that can be coupled to each other such that the plate sections 22 and 24 are movable with respect to each other from a first relative position to a second desired relative position, and subsequently fixed in the desired relative position. In accordance with the illustrated embodiment, the first plate section 22 defines a first body 26, and the second plate section 24 defines a second body 28 having a channel 30 formed therein that is configured to receive the first body 26. The bone fixation plate 20 defines a first outer longitudinal end 32 and a second opposed outer longitudinal end 34 that are longitudinally spaced apart along a central longitudinal axis L-L. During operation, the adaptable fixation plate 20 can be oriented such that the first outer longitudinal end 32 defines a superior end, and the second outer longitudinal end 34 defines an inferior end.

Referring now also to FIGS. 2A-B, the first body 26 of the first plate section 22 extends centrally along a first longitudinal axis 22a, and the second body 28 of the second plate section 24 extends centrally along a second longitudinal axis 24a. In accordance with one embodiment, the first and second plate sections 22 and 24 are fixed such that the longitudinal axes 22a and 24a are substantially aligned along the longitudinal axis L-L of the bone plate 20. The first longitudinal axis 22a extends longitudinally between a first outer longitudinal end 36 and an opposed second outer longitudinal end 38, which can define a superior end and an inferior end, respectively, during use. The first plate section 22 can be positioned superior to the second plate section 24 during operation, such that the superior end 36 of the first plate section 22 likewise defines the superior end 32 of the bone plate 20. The first body 26 further defines a first side wall 52 and an opposed second side wall 54 that extend generally longitudinally between the superior end inferior ends 36 and 38, respectively. The side walls 52 and 54 are separated along the lateral direction A. While the walls 52 and 54 are substantially straight as illustrated, they can alternatively be curved or otherwise shaped as desired.

Referring now to FIGS. 1-5C, the first body 26 includes an insert portion 48 that is configured to be received by the second body 28, and a head portion 50 that is disposed superior with respect to the insert portion 48 and can be configured to attach to an underlying bone such as a vertebral body VB (see FIGS. 10A-C) to which the plate 20 is fixed. The first body 26 further defines laterally opposed ends 40 that define a lateral width W1 therebetween, and opposed inner and outer transverse surfaces 44 and 46, respectively, that define a transverse thickness T1 therebetween. The inner surface 44 is configured to face a vertebral body VB (see FIGS. 10A-C) to which the plate 20 is implanted The inner surface of the head portion 50 can be configured to abut the anterior or anterolateral aspect of the vertebral body VB. The inner and outer surfaces 44 and 46 are substantially flat and extend substantially parallel to each other, though it should be appreciated that the surfaces 44 and 46 could alternatively be curved and can be angularly offset with respect to each other. The width W of the insert portion 48 can be substantially equal to that of the head portion 50. The thickness of the insert portion 48 can be less than that of the head portion 50 as illustrated. In particular, the inner and outer transverse surfaces 44 and 46 of the head portion 50 can extend transversely out from both the inner and outer transverse surfaces 44 and 46, respectively, of the insert portion 48.

The first body 26 further defines a screw hole 56 that extends transversely through the head portion 50. The head portion 50 defines a round inner surface 58 that defines the outer perimeter of the screw hole 56. As will be appreciated from the description below, the inner surface 58 can be curved along the transverse direction T or otherwise shaped so as to receive the head of a bone fixation element, such as a screw. Alternatively or additionally, the hole 56 can be tapered and threaded so as to threadedly mate with a threaded head of a locking screw. The hole 56 can alternatively be unthreaded, and can receive the shaft of a compression screw such that the head of the screw abuts the outer surface 46 of the head portion 50. The screw can thus fasten the first body 26 to the vertebral body VB illustrated in FIG. 10B.

The first body further defines an alignment aperture 60 that extends transversely through the insert portion 48, and is thus disposed inferiorly with respect to the screw hole 56. The insert portion 48 defines an inner surface 62 that defines the outer perimeter of the alignment aperture 60. The inner surface 62 can include laterally extending and longitudinally extending portions, so as to define a substantially square or rectangular shape, though the inner surface 62 can define any alternative shape as desired.

The first body 26 further defines at least one first or inner rib 64, such as a first series or plurality of outer ribs 64 that can be provided as protrusions that extend transversely out from the inner surface 44. The ribs 64 can be parallel to each other and substantially linear, or can be alternatively shaped and spaced as desired. At least one of the inner ribs 64, up to all of the inner ribs 64, can extend laterally and inferiorly in a direction from the second side wall 54 toward the first side wall 52. In particular, at least one of the inner ribs 64, up to all of the inner ribs 64, extends laterally and inferiorly from the second side wall 54 to the first side wall 52. The ribs 64 define a first angle θ1 with respect to the longitudinal axis 22a that can be between 0° and 90°, such as between approximately 5° and approximately 85°, for instance approximately 45°. The ribs 64 are configured to mate with the second plate section 24, as is described in more detail below.

The first body 26 further defines at least one second or outer rib 66, such as a first series or plurality of outer ribs 66 that can be provided as protrusions that extend transversely out from the outer surface 46. The ribs 66 can be parallel to each other and substantially linear, or can be alternatively shaped and spaced as desired. At least one of the outer ribs 66, up to all of the outer ribs 66, can extend laterally and superiorly in a direction from the second side wall 52 toward the first side wall 54. In particular, at least one of the outer ribs 66, up to all of the outer ribs 66, extends laterally and superiorly from the second side wall 54 to the first side wall 52. The ribs 66 define a second angle θ2 with respect to the longitudinal axis 22a that can be between 0° and 90°, such as between approximately 5° and approximately 85°, for instance approximately 45°. It should thus be appreciated that the inner ribs 64 and the outer ribs 66 can be oriented non-parallel with respect to each another such that the ribs 64 and 66 overlap at an intersection 68 when the ribs 64 and 66 are mapped onto a common plane 70, as illustrated in FIG. 3B. For example, the inner ribs 64 and the outer ribs 66 can define an angle al at the intersection 68, which can be any angle between 0° and 90°. In one example, the inner ribs 64 and the outer ribs 66 extend substantially perpendicular to each other. The ribs 64 and 66 can be positioned so as to define a ribbed region 65 that the alignment aperture 60 extends through. The intersections of the ribs 64 and 66 can increase the bending stiffness of the thinned insert portion 48 without a conventional increase in the thickness of that thinned insert portion 48.

Referring now to FIGS. 1-6, the adaptable plate 20 further includes a second plate section 24 that extends centrally along a second longitudinal axis 24a. The second longitudinal axis 24a extends longitudinally between a first outer longitudinal end 72 and an opposed second outer longitudinal end 74, which can define a superior end and an inferior end, respectively, during use. The second plate section 24 can be positioned inferior to the first plate section 22 during operation, such that the inferior end 74 of the second plate section 24 likewise defines the inferior end 34 of the bone plate 20.

The second plate section 24 further defines a second body 28 that, in turn, defines opposed inner and outer transverse surfaces 77 and 79, respectively, that define an outer transverse thickness T2 of the second body 28. The inner surface 77 is configured to face, and in certain embodiments abut, a vertebral body VB (see FIGS. 10A-C) to which the plate 20 is fixed. The transverse thickness T2 of the second body 28 can be substantially equal to the transverse thickness T1 of the head portion 50 of the first body 26. The inner and outer surfaces 77 and 79 are substantially flat and extend substantially parallel to each other, though it should be appreciated that the surfaces 77 and 79 could alternatively be curved and can be angularly offset with respect to each other.

The second body 28 further defines a first side wall 76 and a second laterally opposed side wall 78 that define a lateral width W2 of the second body 28. The width W2 of the second body 28 can be substantially equal to the width W1 of the first body 26. The side walls 76 and 78 extend generally longitudinally between the superior end inferior ends 72 and 74, respectively. During operation, the first side wall 76 is generally aligned with the first side wall 52 of the first plate 22, and the second side wall 78 is generally aligned with the second side wall 54 of the first plate 22. The side walls 76 and 78 are separated along the lateral direction A. While the walls 76 and 78 are substantially straight as illustrated, they can alternatively be curved or otherwise shaped as desired.

The second body 28 includes a receptacle portion 80 that is configured to receive the insert portion 48 of the first body 26, and a head portion 81 that is disposed inferior with respect to the receptacle portion 80. The receptacle portion 80 includes a first or inner arm 82 and a second or outer arm 84 that is spaced transversely from the first arm 82, such that a channel 30 is disposed between the arms 82 and 84. The channel 30 has an initial transverse thickness T3 that is substantially equal to the transverse thickness T1 of the insert portion 48 and less than the transverse thickness T1 of the head portion 50, such that the channel 30 is configured to receive the insert portion 48 of the first plate section 22 when the second plate section 24 is in an initial configuration. The channel 30 is open at the superior end 74 of the second plate 24, such that the inferior end 38 of the first plate 22 can be inserted longitudinally, in an inferior direction, into the superior open end of the channel 30. The laterally opposed sides of the channel 30 can be open as illustrated or closed.

The inner arm 82 defines a first lower or upward-facing interior surface 86 that faces the channel 30, and the outer arm 84 likewise defines a second upper or downward-facing interior surface 88 that faces the channel 30. The surfaces 86 and 88 are substantially flat and extend substantially parallel to each other, though it should be appreciated that the surfaces 86 and 88 could alternatively be curved and can be angularly offset with respect to each other. The thickness T3 of the channel 30 extends between the surfaces 86 and 88, which define the transverse boundary of the channel 30. The outward-facing surface 86 defines at least a first or inner groove 90, such as a first series or plurality of inner grooves 90 that can project into the surface 86. The grooves 90 can be parallel to each other and substantially linear, or can be alternatively shaped and spaced as desired. At least one of the inner grooves 90, up to all of the inner grooves 90, can extend laterally and inferiorly in a direction from the second side wall 78 toward the first side wall 76. In particular, at least one of the inner grooves 90, up to all of the inner grooves 90, extends laterally and inferiorly from the second side wall 78 to the first side wall 76. The inner grooves 90 define a first angle θ3 with respect to the longitudinal axis 24a that can be between 0° and 90°, such as between approximately 5° and approximately 85°, for instance approximately 45°. In this regard, it should be appreciated that the inner grooves 90 can be spaced apart at a sufficient distance so as to mate with, or receive, the inner ribs 64 of the first plate section 22.

The outer arm 84 likewise defines a second or outer groove 92, such as a second series or plurality of outer grooves 92 that can project into the interior surface 88. The grooves 92 can be parallel to each other and substantially linear, or can be alternatively shaped and spaced as desired. At least one of the outer grooves 92, up to all of the outer grooves 92, extends laterally and superiorly in a direction from the from the second side wall 78 to the first side wall 76. In particular, at least one of the outer grooves 92, up to all of the outer grooves, extends laterally and superiorly from the second side wall 78 to the first side wall 76. The grooves 92 define a second angle θ4 with respect to the longitudinal axis 24a that can be between 0° and 90°, such as between approximately 5° and approximately 85°, for instance approximately 45°.

Figure 3A:
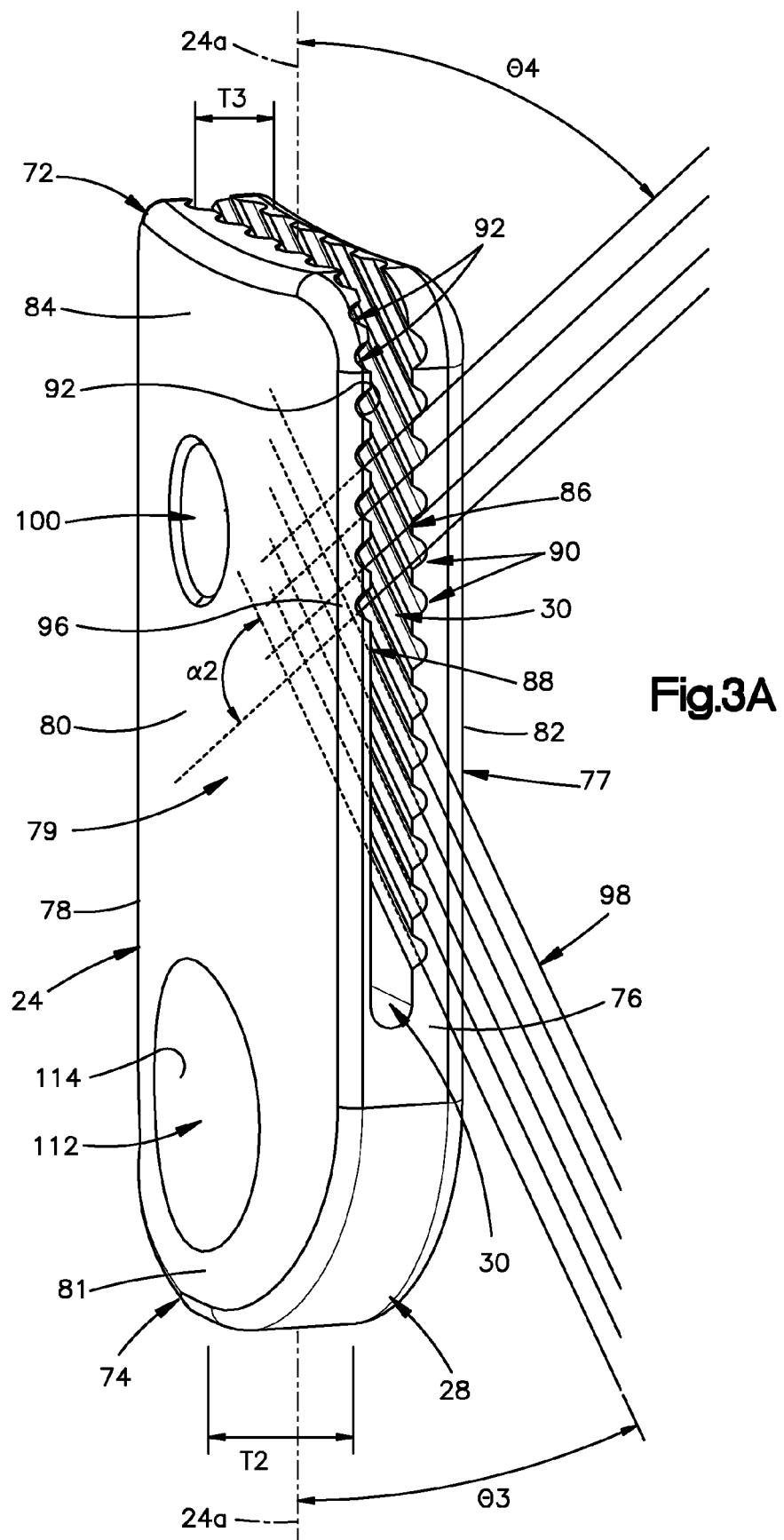
FIG. 3A is a perspective view of the second plate section illustrated in FIGS. 1A-B.
Figure 3B:
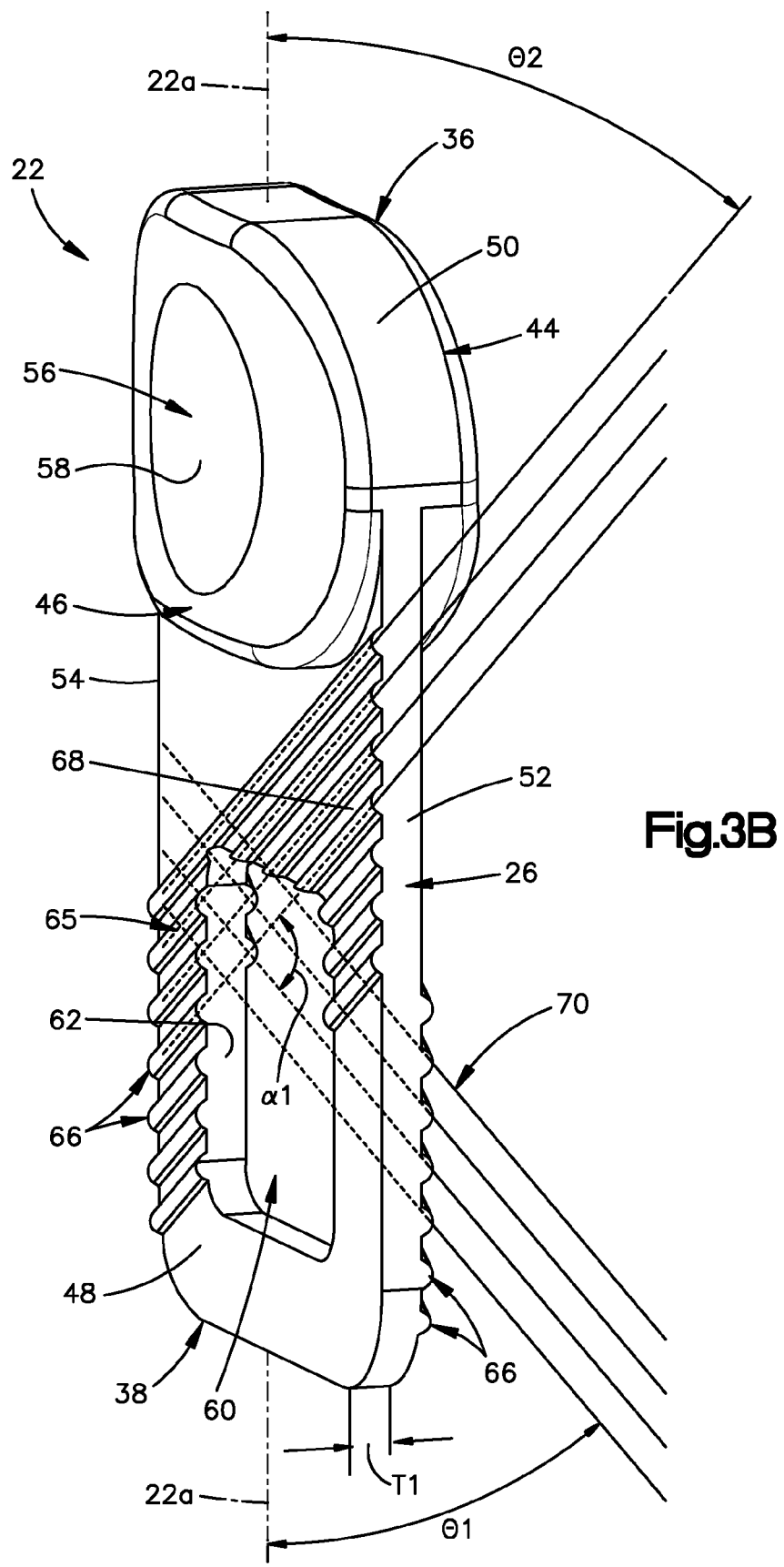
FIG. 3B is a perspective view of the first plate section illustrated in FIGS. 1A-B.
Figure 4B:
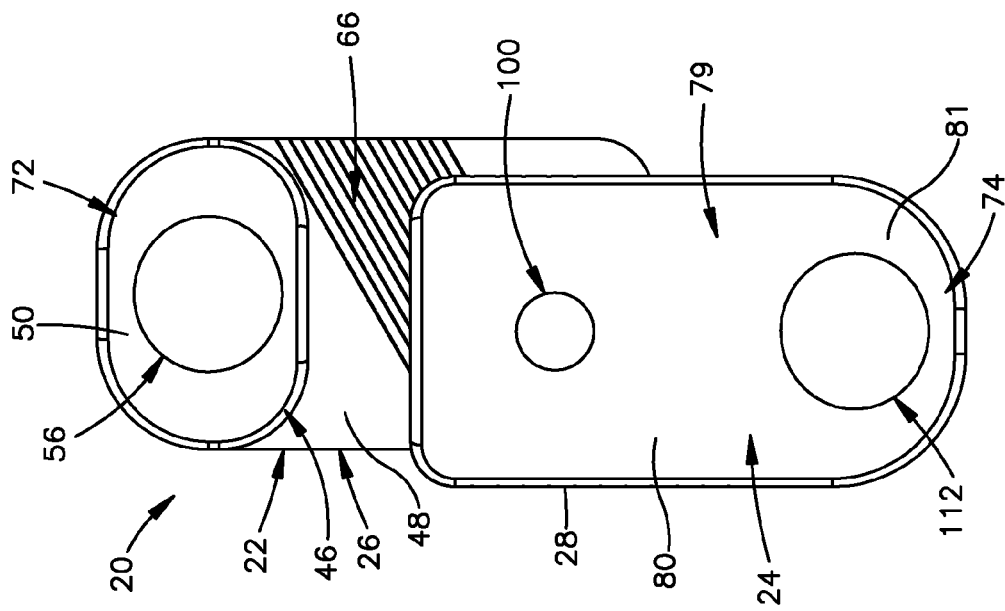
FIG. 4B is a top plan view of the adaptable fixation plate similar to FIG. 4A, but showing the plate sections offset with respect to each other.
Figure 4A:
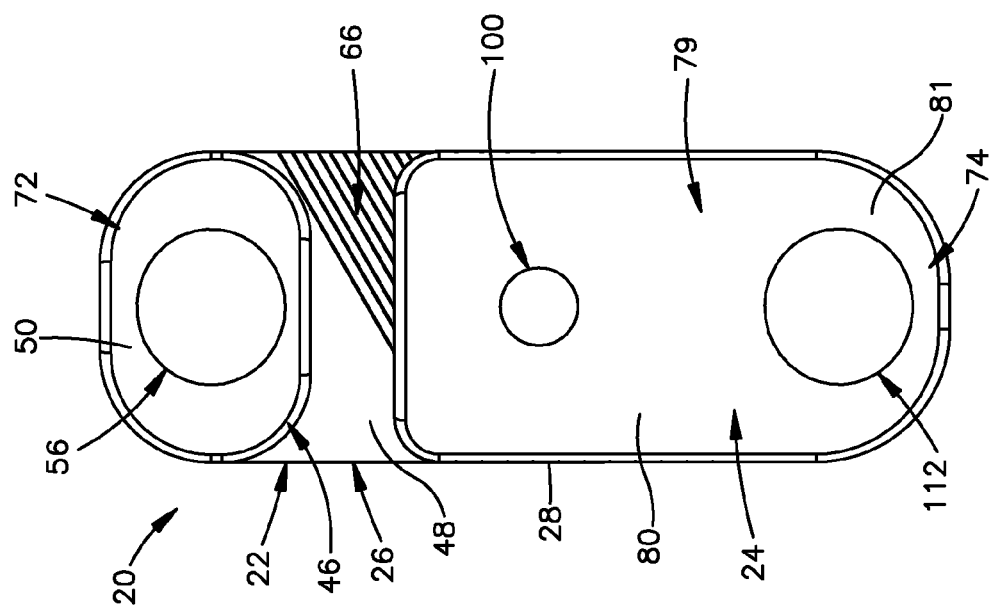
FIG. 4A is a top plan view of the adaptable fixation plate illustrated in FIGS. 1A-B.
Figure 4D:
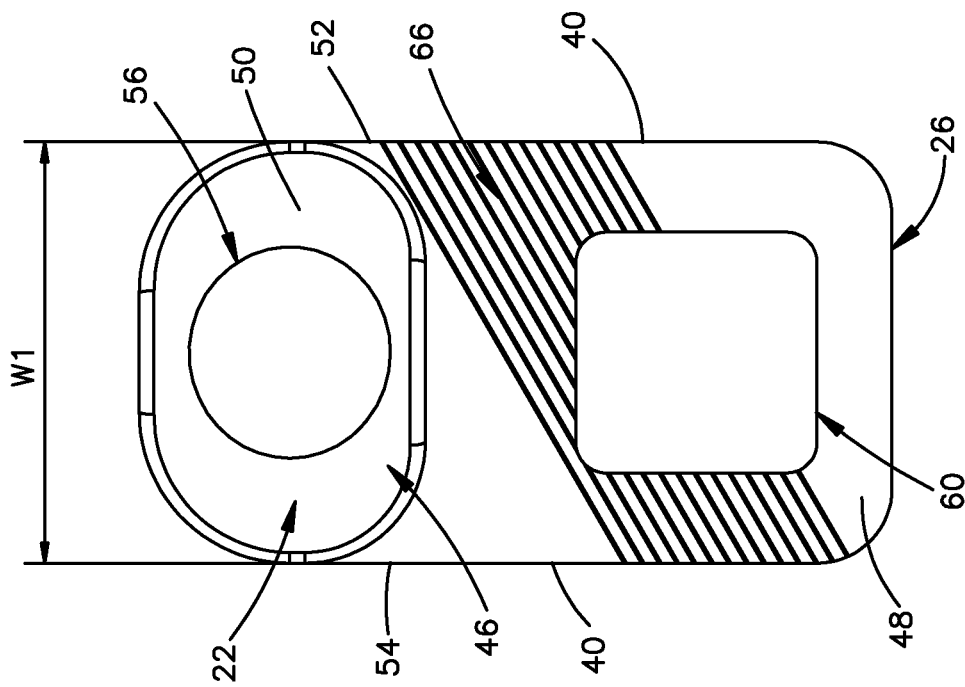
FIG. 4D is a top plan view of the first plate section of the adaptable fixation plate illustrated in FIG. 4A.
Figure 4C:
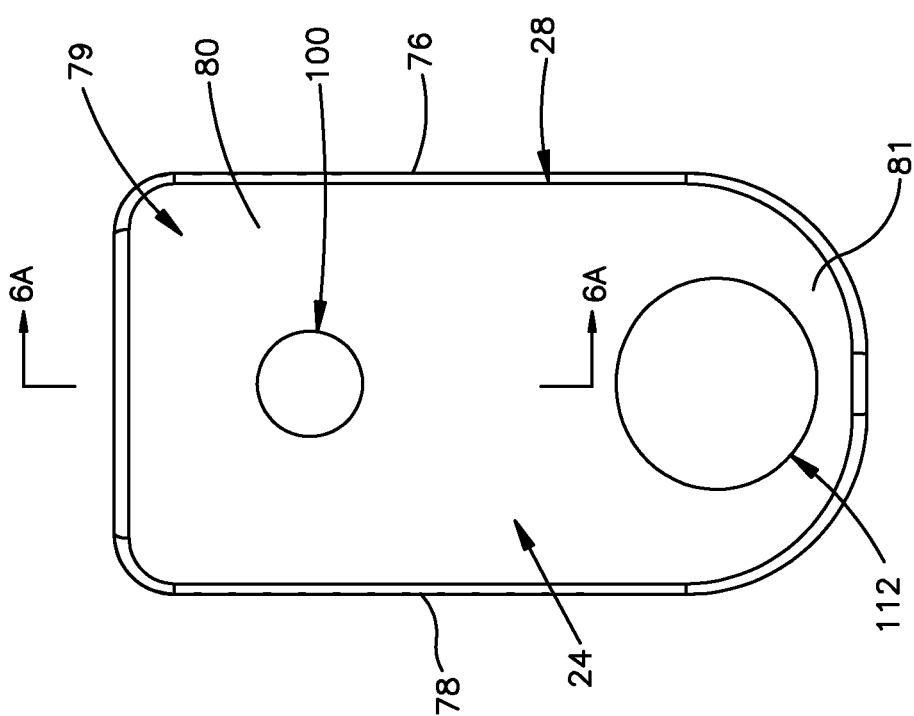
FIG. 4C is a top plan view of the second plate section of the adaptable fixation plate illustrated in FIG. 4A.

The inner grooves 90 and the outer grooves 92 can thus be oriented non-parallel with respect to each another such that the ribs grooves 92 and 94 overlap at an intersection 96 when the grooves 92 and 94 are mapped onto a common plane 98, as illustrated in FIG. 3A. For example, the inner grooves 90 and the outer grooves 92 can define an angle α2 at the intersection 96, which can be any angle between 0° and 90°. In one example, the inner grooves 90 and the outer grooves 92 extend substantially perpendicular to each other. It should be appreciated that the inner and outer grooves 90 and 92 are sized and spaced to receive the inner and outer ribs 64 and 66, respectively. Because the grooves 90 and 92 are non-parallel to each other, and the ribs 64 and 66 are non-parallel to each other, the inner and outer plate sections 22 and 24 is locked with respect to relative movement when the ribs 64 and 66 are disposed in the grooves 90 and 92. For instance, the engagement of the grooves 90 and ribs 64 prevents the ribs 66 from translating within the grooves 92. Likewise, the engagement of the grooves 92 and the ribs 66 prevents the ribs 64 from translating within the grooves 90.

Figure 6A:
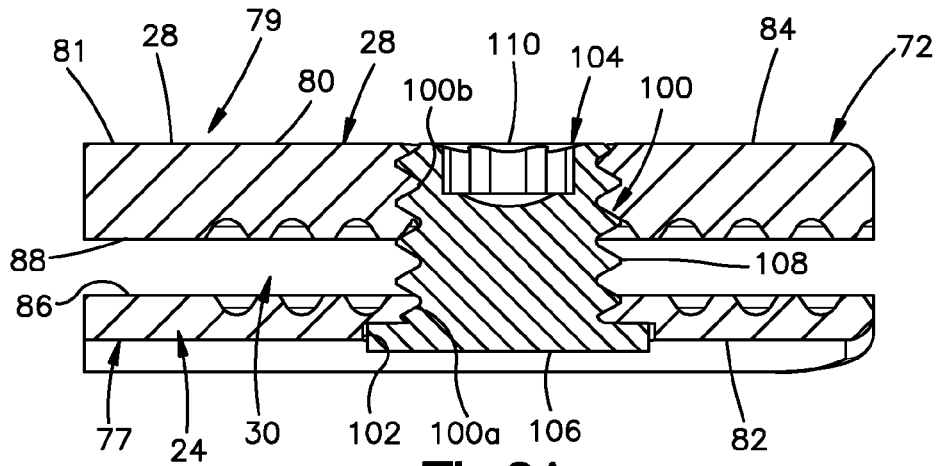
FIG. 6A is a schematic sectional side elevation view of the second plate segment illustrated in FIG. 4C, taken along line 6A-6A, showing a locking fastener mounted to the second plate section.

Referring now also to FIG. 6A, the second plate 24 includes a transverse locking aperture 100 extending through the second body 28. In particular, the locking aperture includes a first or inner portion 100a extending through the inner arm 82, and a second or outer portion 100b extending through the outer arm 84. The inner portion 100a can include a counterbore 102 at its proximal end that extends into the inner transverse surface 77 and has a diameter greater than the distal portion of the aperture 100. The distal portion of the aperture 100 can be threaded in both the first portion 100a and the second portion 100b.

Figure 6B:
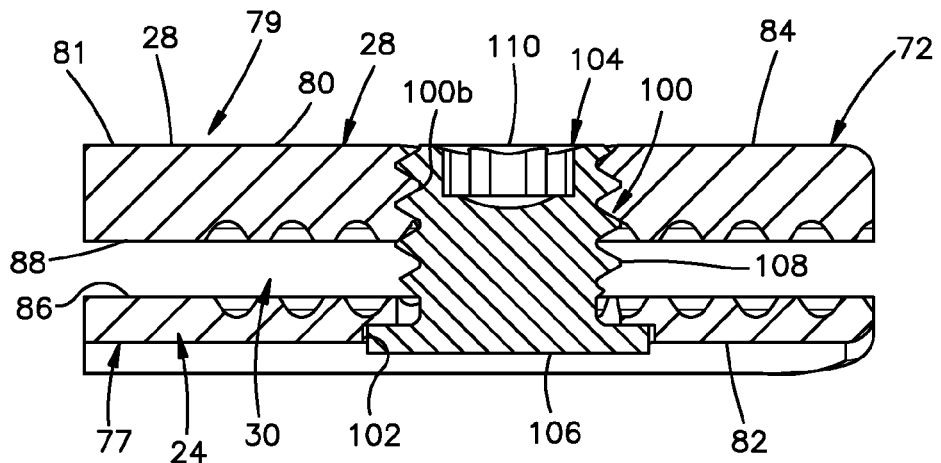
FIG. 6B is a schematic sectional side elevation view similar to FIG. 6A, but showing the second plate section constructed in accordance with an alternative embodiment.
Figure 6C:
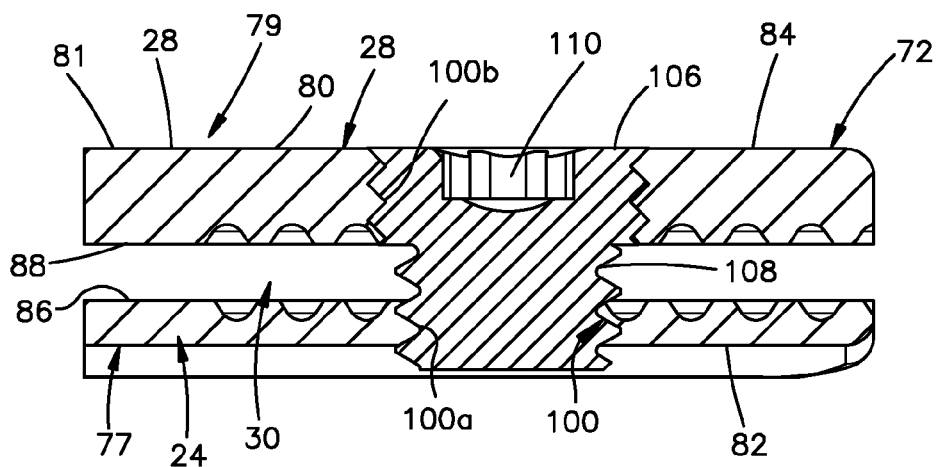
FIG. 6C is another schematic sectional side elevation view similar to FIG. 6A, but showing the second plate section constructed in accordance with an alternative embodiment.

The locking aperture 100 can be aligned with the alignment aperture 60 of the first plate section 22 during operation. Accordingly, during operation, the plate 20 can further include a fastener 104 that is configured to lock the first and second plate sections 22 and 24 together. The fastener 104 can be a screw, a screw and nut, a pair of screws coupled to provide a clamping arrangement, a rivet, a pin, a clamping member, or other suitable mechanism. As illustrated, the fastener 104 includes a head portion 106 and a threaded shaft portion 108 extending distally from the head portion 106. The head portion 106 is configured to be seated in the counterbore 102 such that the head 106 is flush or recessed with respect to the inner surface 77 of the second body 28. The threaded shaft 108 is configured to mate with the threaded hole portions 100a and 100b to lock the first and second arms 82 and 84 with respect to movement in the transverse direction. The shaft 108 defines an outer transverse surface that includes a cruciform or alternative geometric key 110 formed therein that is configured to receive a driving instrument that can engage the key 110 so as to rotatable drive the fastener 104 within the opening 100. Referring now to FIG. 6B, in accordance with another embodiment, the head portion 106 and the portion of the shaft portion 108 disposed proximate to the head portion 106 is unthreaded, such that the fastener 104 does not threadedly engage the inner arm 82, but rather threadedly engages the outer arm 84 so as to compress the arms 82 and 84 against the first plate section 22. Referring now to FIG. 6C, in accordance with yet another embodiment, the outer opening portion 100b has a diameter sized to receive the head 106, which is threaded. The head 106 further includes the key 110.

During operation, the insert portion 48 of the first plate section 22 is inserted into the channel 30 of the second plate section 24. Because the transverse thickness between the inner and outer surfaces 44 and 46 is substantially equal to that between the interior surfaces 86 and 88, and because the ribs 64 and 66 project out from the surfaces 44 and 46, the ribs 64 and 66 cause the arms 82 and 84 to flex transversely away from each other as the insert portion 48 is inserted into the channel 30 until the ribs 64 and 66 are disposed in respective grooves 90 and 92, at which point the arms 82 and 84 return to their normal or substantially planar orientation. In this regard, it should be appreciated that each of the interior surfaces 86 and 88 of the arms 82 and 84 and the respective surfaces 44 and 46 of the insert portion 48 can define a ratchet. The insert portion 48 is translated longitudinally into the channel 30 until the plate 20 has a desired length, at which point the fastener 104 can be tightened in the opening 100, thereby preventing the arms 82 and 84 from flexing away from each other, and locking the position of the first plate section 22 with respect to the second plate section 24.

Referring again to FIGS. 1-5C, the second body 28 further defines a screw hole 112 that extends transversely through the head portion 81. The head portion 81 defines a round inner surface 114 that defines the outer perimeter of the screw hole 112. As will be appreciated from the description below, the inner surface 114 can be curved along the transverse direction T or otherwise shaped so as to receive the head of a bone fixation element, such as a screw. Alternatively or additionally, the hole 112 can be tapered and threaded so as to threadedly mate with a threaded head of a locking screw. The hole 112 can alternatively be unthreaded, and can receive the shaft of a compression screw such that the head of the screw abuts the outer surface 79 of the head portion 81. The screw can thus fasten the second body 28 to the vertebral body VB illustrated in FIG. 10B.

Referring now to FIGS. 7A-10C, in the illustrated embodiment, the bone fixation system includes the adaptable plate 20 and an anchor-in-anchor bone fixation system 120 similar to the anchor-in-anchor bone anchoring system described in detail in U.S. patent application Ser. No. 12/631,293 filed Dec. 4, 2009, the disclosure of which is hereby incorporated by reference as if set forth in its entirety herein. In particular, the bone fixation system 120 includes a first or primary bone anchor provided as an anterior pedicle screw 122 having a first anterior pedicle screw head portion 124 that is couplable to the first screw hole 56 and a first auxiliary bone anchor or locking bone anchor provided as a head screw 126 having a first locking head screw head portion 128 couplable to a hole formed through the first anterior pedicle screw head portion 124.

Figure 11:
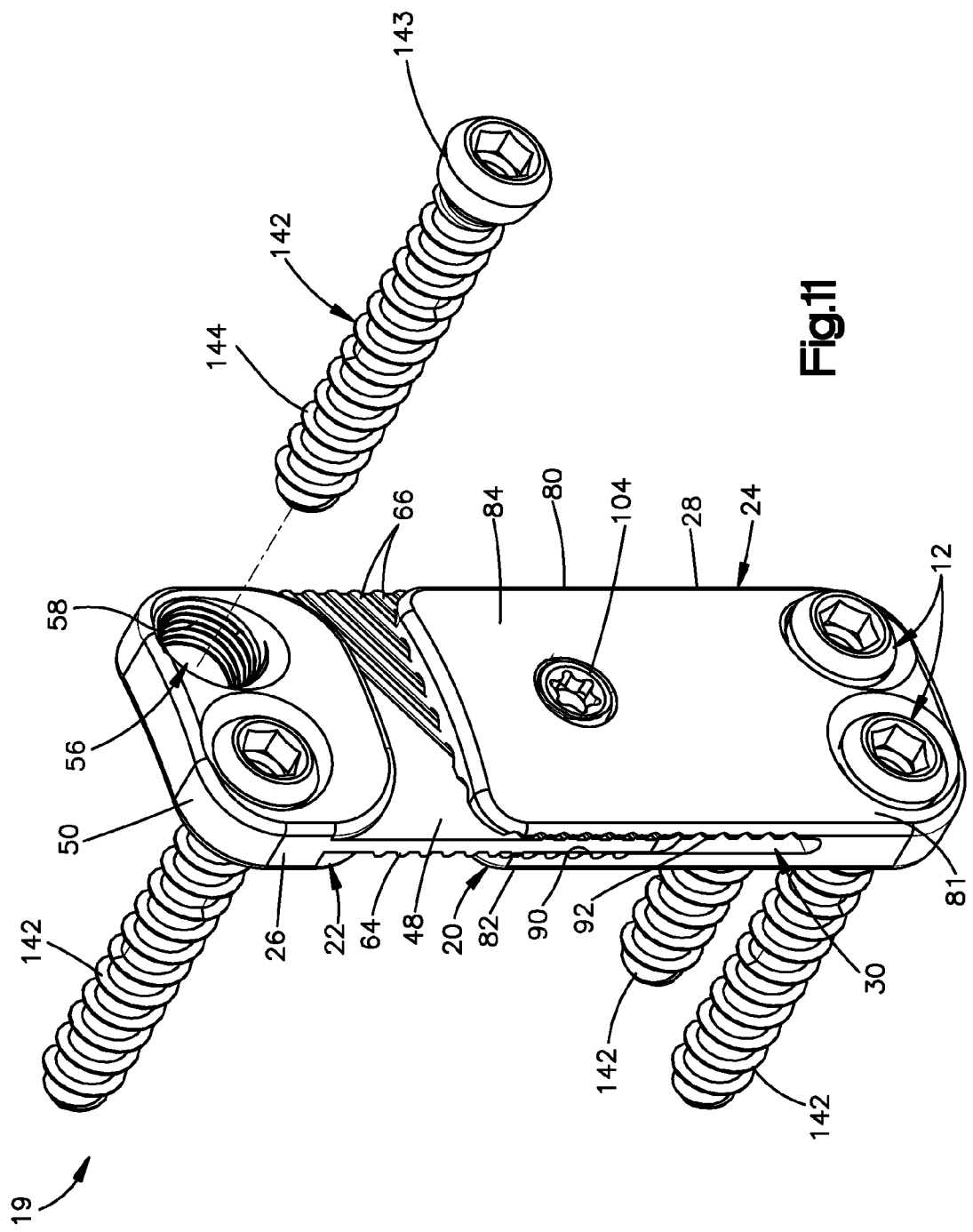
FIG. 11 illustrates a top perspective view of an adaptable fixation plate constructed in accordance with an alternative embodiment.

Similarly, the bone fixation system 120 includes a second primary bone anchor or anterior pedicle screw 130 having a second anterior pedicle screw head portion 132 that is couplable to the second screw hole 140 and a second auxiliary bone anchor or locking head screw 133 having a second locking head screw head portion 135 couplable to a hole formed through the second anterior pedicle screw head portion 132. The first and second anterior pedicle screws 122 and 130 are configured to be delivered anteriorly through the vertebral body VB, extend distally through the vertebral body VB and at least partially into the pedicle region of the posterior of the vertebral body VB. The inclusion of the first and second anterior pedicle screws 122 and 130 can provide for the capture of two cortical surfaces of the vertebral bodies VB with the shafts of each of the first and second anterior pedicle screws 122 and 130. The bone fixation system 120 described herein in reference to the illustrated combines the advantages of an anterior approach to the spine with the biomechanical characteristics of cervical screw fixation using a single approach. Further, the bone fixation system 120 provides two bone fixation elements through a single screw hole, thereby allowing for a single screw hole at the head of each plate section, and allowing the width of the adaptable plate 20 to be reduced. Each anterior pedicle screw heads 124 and 132 defines a respective threaded aperture 134 and 136, such that the threading is configured to mate with respective exterior threading 138 and 140 on the first and second locking head screw heads 128, 135, respectively. Alternatively, shorter, more conventional anterior plate screws can be included in superior and inferior pairs, as is described below in reference to FIGS. 11-13.

The first and second plate sections 22 and 24, as well as the first and second anterior pedicle screws 122, 130, the first and second locking head screws 124, 132, and the fastener 104, can be formed from a variety of biocompatible materials, including titanium and its alloys, stainless steel, and polymers such as PEEK. The series of ribs 64 and the series of distal ribs 66 as well as the grooves 90 and 92 can be machined into the first and second plate sections 22 and 24 in a number of ways, including milling, wire electrical discharge machining (wire EDM), or selective laser melting techniques.

In operation, and in reference to FIGS. 1-10C, the adaptable plate 20 provides inferior, as well as lateral, plate adjustability so as to adjust a position of the screw holes 56 and 112 to a desired location, as well as the first and second plate sections 22, 24, with respect to the first and second anterior pedicle screws 122 and 130. Pilot holes for the first and second anterior pedicle screws 122 and 130 can be drilled prior to the insertion of the first and second anterior pedicle screws 122 and 130 into the respective vertebral body VB. The first and second anterior pedicle screws 122 and 130 are implanted through the anterior surface of the adjacent vertebral bodies VB and extend distally into the pedicle region of the posterior of the vertebral bodies VB. The first plate section 22 is provisionally coupled to the second plate section 24 by inserting the insert portion of the first plate section 22 between the arms 82 and 84 and into the channel 30 of the second plate section 24 such that the locking hole 100 is aligned with the alignment aperture 60, and such that at least a portion of the series of the ribs 64 and 66 engages at least a portion of the corresponding grooves 90 and 92, respectively. The first and second plate sections 22 and 24 are then adjusted with respect to one another in both the superior-inferior direction as well as the lateral direction until the screw holes 56 and 112 are positioned as desired with respect to the orientation of the first and second anterior pedicle screws 122 and 130. It should thus be appreciated that the insert portion 48 may or may not be centrally located on the longitudinal axis 24a of the second plate section 24 during operation.

Figure 9A:
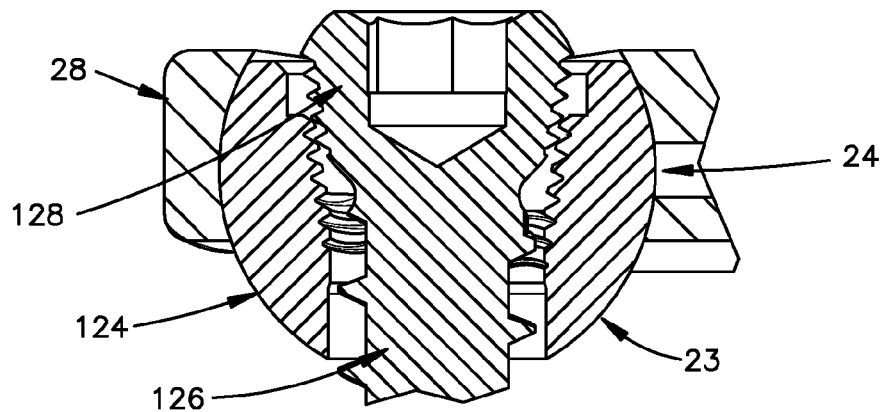
FIGS. 9A-C are magnified sectional elevation views illustrating a method for locking one of the anchors of the anchor-in-anchor fixation system illustrated in FIGS. 8A-D to the adaptable plate.
Figure 9B:
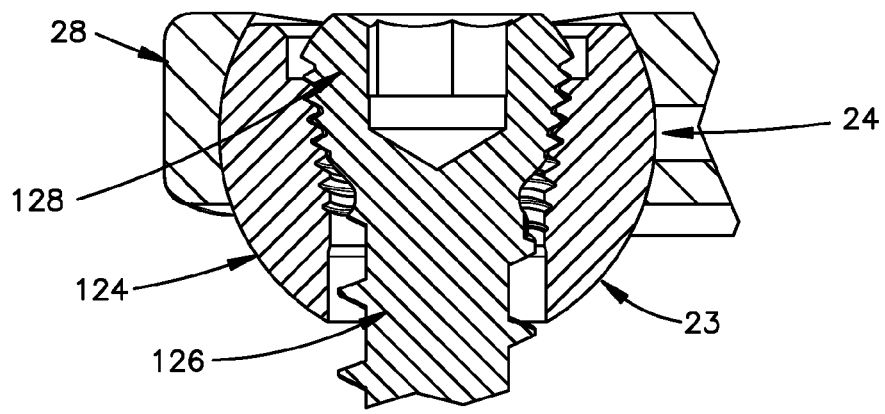
Figure 9C:
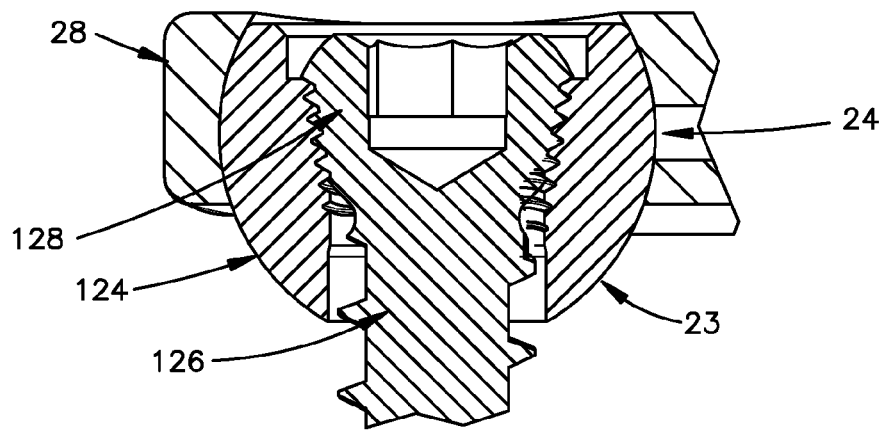

The first and second plate sections 22 and 24 can be coupled to the first and second anterior pedicle screws 122 and 130, respectively, by snapping the first and second anterior pedicle screw heads 124 and 132 into the first and second screw holes 56 and 112. The first and second locking head screws 128 and 133 are then inserted through the first and second anterior pedicle screw heads 124 and 132 such that the exterior threading on the first and second locking head screw heads 128 and 135 engages the interior threading on the anterior pedicle screw heads 124 and 132. The advancement of the first and second locking head screw heads 128 and 189 through the first and second anterior pedicle screw heads 124 and 132 causes an outward expansion of the anterior pedicle screw heads 124 and 132 and a frictional locking of the first and second anterior pedicle screw heads 124 and 132 against the surfaces 58 and 114 of the screw holes 56 and 112, as illustrated in FIGS. 9A-C. The desired orientation of the first plate section 22 with respect to the second plate section 24 is locked when the fastener 104 is locked in the locking hole 100, which clamps the arms 80 and 82 of the second plate section 22 onto the insert portion 48 of the first plate section 22, such that the insert portion 48 is retained within the channel 30.

The angle defined between the series of proximal ribs 64 and 66 and, correspondingly, the angle defined between the grooves 90 and 92, as well as the distance between each rib 64 and each rib 66 and, correspondingly, the distance between each groove 90 and each groove 92, can define the step size of adaptability in both the superior-inferior (cranial-caudal) direction as well as the lateral direction, and can be tailored to a number of appropriate ranges of adaptability to meet the desired requirements for anterior spinal stabilization.

The adaptable plate 20 can provide the flexibility to choose the desired orientation of the first and second plate sections 22 and 24 with respect to a patient's anatomy prior to the insertion of the first and second anterior pedicle screws 122 and 130 or, alternately, to insert the first and second anterior pedicle screws 122 and 130 and allow the orientation of the first and second anterior pedicle screws 122 and 130 to determine the desired position and orientation of the first and second plate sections 22 and 24.

It should be appreciated that the adaptable plate 20 can alternatively include the ribs 64 and grooves 90 without the ribs 66 and grooves 92, or alternatively can include the ribs 66 and grooves 92 without the ribs 64 and grooves 90. It should be further appreciated that the ribs 64 and 66, as well as the grooves 90 and 92, can assume any desired shape, such as a series of protrusions and indentations assuming a variety of geometries, including cylindrical protrusions and indentations, semi-spherical protrusions and indentations, cubic protrusions and indentations, triangular or pyramidal protrusions and indentations, or the like.

Furthermore, while the series of ribs 64 and 66, and the corresponding grooves 90 and 92, are oriented obliquely with respect to the longitudinal axis L-L of the adaptable plate 20, it should be appreciated that the ribs 64 and 66, and the grooves 90 and 92, respectively, can be oriented parallel and/or perpendicular to the longitudinal axis L-L, or at any desired angulation therebetween. Furthermore, while the ribs 64 and 66 intersect at a perpendicular angle as illustrated, it should be appreciated that the ribs 64 and 66 can alternatively intersect at any desired angle between 0° and 90°, or can be disposed at different regions of the first plate section 22 so as to not overlap or crisscross at all.

It should be appreciated that the adaptable bone fixation plate 20 has been illustrated and described in accordance with one embodiment, and that numerous alternative embodiments are envisioned. For instance, referring now to FIG. 11, the adaptable plate 20 includes a pair of screw holes 56 extending through the head portion 50 of the first plate section 22, and a pair of screw holes 112 extending through the head portion 81 of the second plate section 24. The plate sections 22 and 24 are otherwise constructed as described above. The screw holes 56 can be disposed laterally adjacent to each other and laterally aligned with each other, or can be offset from each other along the longitudinal axis L. Alternatively still, the screw holes 56 can be longitudinally aligned with each other. It should be appreciated that the first plate section 22 can alternatively include any number of screw holes 56 as desired. Thus, the plate section includes at least one screw hole 56, such as a plurality of screw holes. Likewise, the screw holes 112 can be disposed laterally adjacent to each other and laterally aligned with each other, or can be offset from each other along the longitudinal axis L. Alternatively still, the screw holes 112 can be longitudinally aligned with each other. It should be appreciated that the first plate section 22 can alternatively include any number of screw holes 112 as desired. Thus, the plate section includes at least one screw hole 112, such as a plurality of screw holes.

Furthermore, the interior surfaces 58 of one up to all of the screw holes 56 can be threaded or have a portion that is threaded. Likewise, the interior surfaces 114 of one up to all of the screw holes 112 can be threaded or have a portion that is threaded. Thus, the bone fixation system 19 can include single bone anchors 142 having respective head portions 143 and shaft portions 144 extending from the head portions 143. The shaft portions 144 can be threaded as illustrated so as to purchase with the underlying vertebral body VB. Furthermore, the head portion 143 can define external threads on its outer circumferential surface. The head portion 143 and the inner surfaces 114 and 58 can be tapered along the direction of bone anchor insertion. Thus, the bone anchors 143 can lock against the plate sections 22 and 24. Alternatively, the bone anchor head portions 143 can be unthreaded and/or the screw holes 56 and 112, or a portion of the screw holes 56 and 112 can be unthreaded, such that the head portions 56 and 112 compress the adaptable plate 20 against the underlying vertebral bodies VB.

Figure 12:
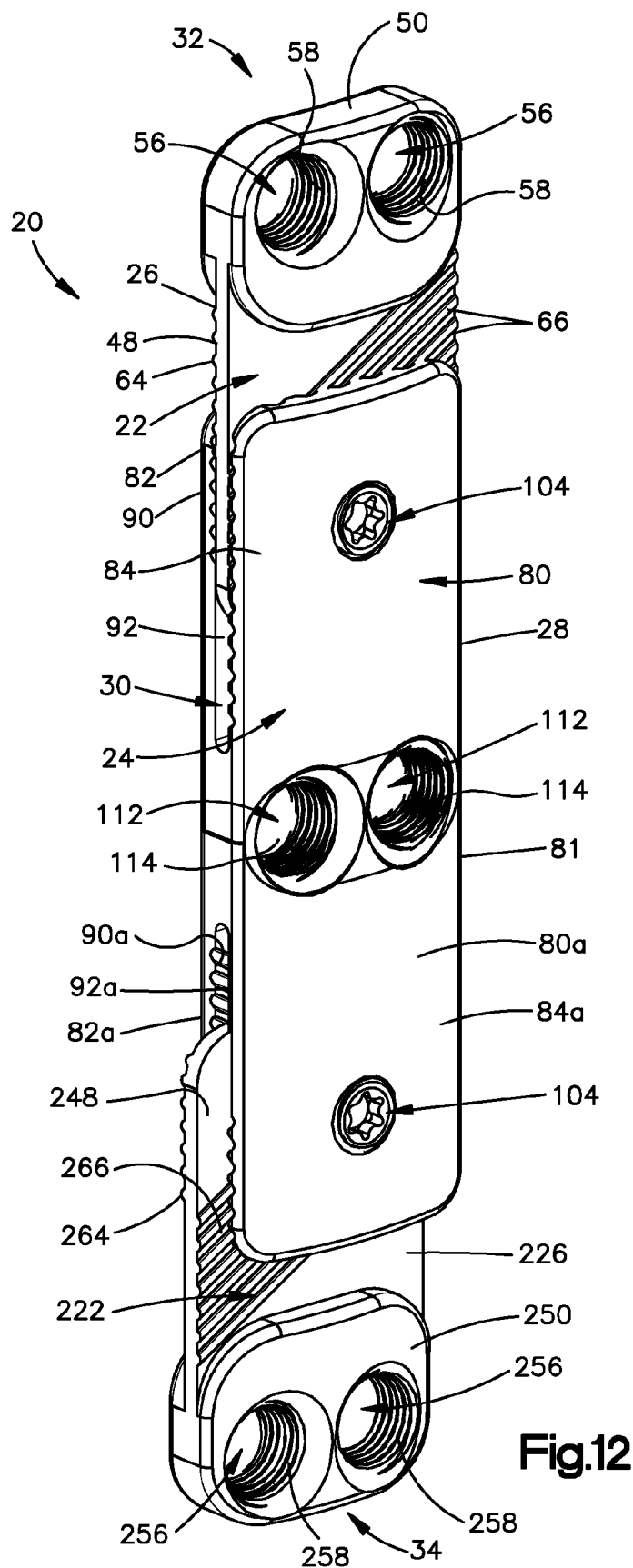
FIG. 12 is a perspective view of an adaptable fixation plate constructed in accordance an alternative embodiment.
Figure 13:
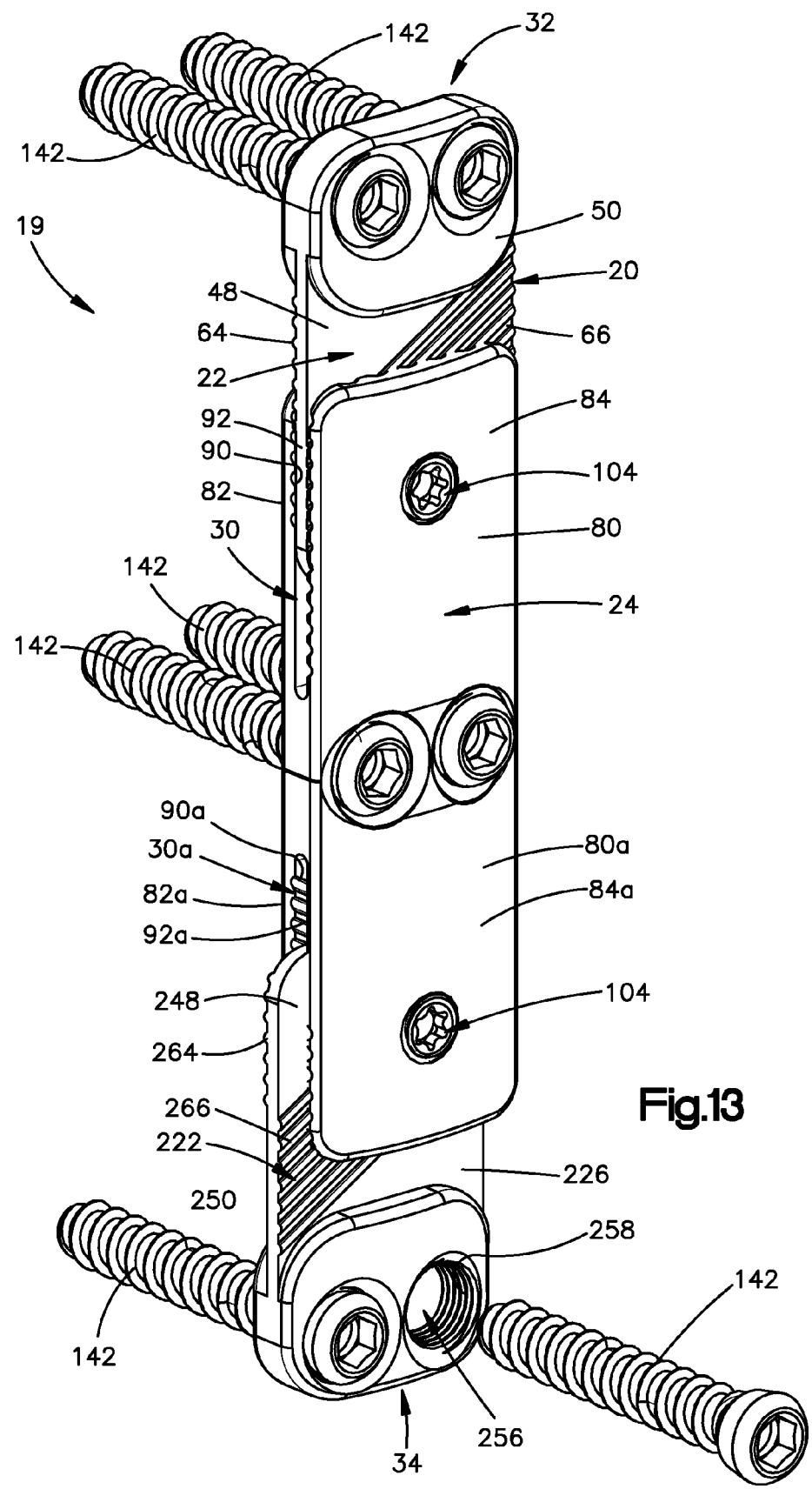
FIG. 13 is a perspective view of a bone fixation system constructed in accordance with an alternative embodiment, including the adaptable fixation plate illustrated in FIG. 12 and bone anchors or screws mounted to the plate.

Referring now to FIGS. 12-13, the adaptable plate 20 can include the first plate section 22, the second plate section 24, and a third plate section 222 that includes reference numerals corresponding to those of the first plate section 22 incremented by 200 for the purposes of form and clarity. Thus, the third plate section 222 can be constructed as described above with respect to the first plate section 22 unless otherwise indicated. Accordingly, as illustrated, the third plate section 222 includes a third body 226 that defines an insert portion 248 and a head portion 250. The insert portion 248 is disposed superior with respect to the head portion 250, such that the head portion 250 defines the inferior end 34 of the bone plate 20. The insert portion 248 defines intersecting and overlapping ribs 264 and 266 as described above with respect to the ribs 64 and 66 of the first plate section 22. The head portion 250 includes a pair of screw holes 56 as described above with respect to FIG. 11, though it should be appreciated that the head portion 250 can alternatively include a single screw hole 56 as described above with respect to FIGS. 1A-B.

Accordingly, the second plate portion 24 defines a second receptacle portion 80a that is constructed as described above with respect to the receptacle portion 80 unless otherwise indicated. Thus, the head portion 81 is disposed longitudinally between the receptacle portions 80 and 80a. The second receptacle portion 80a defines a second channel 30a having an open end at the inferior end of the second body 26a. The second channel 30a is disposed superior with respect to the third plate section 222, and is configured to receive the insert portion 248 of the third body 226 in the manner described above. The second receptacle portion 80a includes first and second arms 82a and 84a that present corresponding inner grooves 90a and 92a that overlap and intersect as described above. The grooves 90a and 92a are thus configured to mate with the ribs 264 and 266 of the third body 226. The second plate section further includes a second fastener 104 that can be actuated so as to lock the third plate 222 in the second receptacle 30a in the manner described above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. A bone fixation system configured to be fixed to at least one underlying bone, the bone fixation system comprising:
a first plate section defining a first body that extends along a central axis between a superior end and an inferior end such that the superior end and the inferior end are spaced from each other in an inferior-superior direction, the first body defining a first side wall and a second side wall that each extend between the superior end and the inferior end such that the first side wall and the second side wall are spaced from each other in a lateral direction, the first body defining opposed inner and outer surfaces and a screw hole extending through the inner and outer surfaces, and the first body including at least one first rib extending from at least one of the inner and outer surfaces;
a second plate section defining a second body that extends along a central axis between a superior end and an inferior end, the second body defining a channel configured to receive a portion of the first body such that the first body is initially translatable within the channel along both the inferior-superior direction and the lateral direction, the channel defined by opposed interior surfaces, wherein the second body defines at least one groove extending into at least one of the interior surfaces, the at least one groove being configured to mate with the at least one rib;
a fastener configured to lock the rib in the groove so as to prevent the first plate section from translating relative to the second plate section.

2. The bone fixation system as recited in claim 1, wherein the first plate section defines a plurality of ribs extending from one of the inner and outer surfaces.

3. The bone fixation system as recited in claim 2, wherein each of the plurality of ribs extends substantially parallel to each other.

4. The bone fixation system as recited in claim 1, wherein the second plate section defines a plurality of grooves extending into one of the interior surfaces.

5. The bone fixation system as recited in claim 4, wherein each of the plurality of grooves extends substantially parallel to each other.

6. The bone fixation system as recited in claim 1, wherein the rib is a first rib, and the first plate section further comprises at least one second rib extending from the other of the inner and outer surfaces.

7. The bone fixation system as recited in claim 6, wherein the first and second ribs overlap at an intersection when mapped onto a common plane.

8. The bone fixation system as recited in claim 7, wherein the first and second ribs extend substantially perpendicular to each other.

9. The bone fixation system as recited in claim 6, wherein the groove is a first groove, and the second plate section further comprises at least one second groove extending into the other of the interior surfaces, the second groove configured to mate with the second rib.

10. The bone fixation system as recited in claim 1, wherein the first plate section defines an alignment aperture extending through the inner and outer surfaces of the first body, and the second plate section comprises a locking aperture aligned with the alignment aperture, the locking aperture configured to receive the fastener so as to lock the rib in the groove.

11. The bone fixation system as recited in claim 10, wherein the second body defines a pair of arms spaced apart, each arm defining one of the interior surfaces.

12. The bone fixation system as recited in claim 1, wherein the first plate section defines a head portion and an insert portion, the head portion defining a thickness between the inner and outer surfaces that is greater than that of the insert portion, and the insert portion carrying the at least one rib.

13. The bone fixation system as recited in claim 12, wherein the thickness of the head portion is greater than that of the channel.

14. The bone fixation system as recited in claim 12, wherein the thickness of the insert portion is substantially equal to the thickness of the channel, such that the arms flex outward when the at least one rib is disposed in the channel but not mated with the at least one groove.

15. The bone fixation system as recited in claim 12, wherein the second body defines a head portion and a receptacle portion, the receptacle portion defining the channel, the head portion of the second body defining a screw hole, and the head portion of the first body defining a screw hole.

16. The bone fixation system as recited in claim 15, further comprising at least one first plate bone screw configured to extend through the head portion of the first body, and a second bone screw configured to extend through the head portion of the second body.

17. The bone fixation system as recited in claim 15, further comprising an anchor-in-anchor bone fixation system extending through the screw holes.

18. The bone fixation system as recited in claim 15, wherein the channel is a first channel, and the second body defines a second channel, such that the first channel extends into a superior end of the second body, and the second channel extends into an inferior end of the second body, the second channel defined by a pair of opposed interior surfaces, at least one of the interior surfaces having a groove formed therein.

19. The bone fixation system as recited in claim 18, further comprising a third plate section defining a third body that extends along a central axis that extends between a superior end and an inferior end, the third body defining opposed inner and outer surfaces and a screw hole extending through the inner and outer surfaces, and the third body including at least one rib extending from one of the inner and outer surfaces and configured to mate with the groove of the second channel so as to prevent the third plate section from translating with respect to the second plate section.

20. The bone fixation system as recited in claim 15, wherein the head portions of the first and second bodies define a pair of adjacent screw holes.

21. The bone fixation system as recited in claim 1, wherein the opposed interior surfaces are substantially flat.

22. The bone fixation system as recited in claim 1, wherein the opposed interior surfaces extend parallel to each other.

23. The bone fixation system as recited in claim 1, wherein the opposed inner and outer surfaces are substantially flat.

24. The bone fixation system as recited in claim 1, wherein the opposed inner and outer surfaces are substantially parallel to each other.

25. The bone fixation system as recited in claim 1, wherein the at least one rib extends laterally and inferiorly from the first side wall to the second side wall.

26. The bone fixation system as recited in claim 25, wherein the rib is substantially linear.

27. The bone fixation system as recited in claim 1, wherein the first body includes a plurality of ribs that extend from both of the inner and outer surfaces, and the ribs that extend from the inner surface are oriented non-parallel with respect to the ribs that extend from the outer surface.

28. A bone fixation plate configured to be fixed to at least one underlying bone, the bone fixation plate comprising:
　a first plate section defining a first body that defines a first side wall and a second side wall that are spaced from each other in a lateral direction, the first body extends along a central axis that extends between a superior end and an inferior end such that the superior end is spaced from the inferior end in a superior direction, and the inferior end is spaced from the superior end in an inferior direction, the first body defining i) opposed inner and outer surfaces defining a thickness therebetween, ii) a head portion and an insert portion, wherein the thickness of the head portion is greater than the thickness of the insert portion, iii) a first plurality of ribs projecting from the inner surface of the insert portion and extending in the lateral direction and in the inferior direction in a direction from the second side wall toward the first side wall, iv) a second plurality of ribs projecting from the outer surface of the insert portion and extending in the lateral direction and in the superior direction in a direction from the second side wall toward the first side wall, and v) at least one screw hole extending through the head portion;
　a second plate section defining a second body that extends along a central axis between a superior end and an inferior end, the second body defining a receptacle portion and a head portion,
　　the head portion defining at least one screw hole extending therethrough; and
　　the receptacle portion including first and second arms that are spaced so as to present respective first and second interior surfaces that define a channel therebetween, the first arm including a first plurality of grooves extending into the corresponding inner surface, the second arm including a second plurality of grooves extending into the corresponding inner surface, wherein the first and second pluralities of grooves are configured to mate with the first and second pluralities of ribs so as to lock the first and second plate sections with respect to relative movement.

29. The bone fixation plate as recited in claim 28, wherein the first and second pluralities of ribs overlap and intersect when mapped on a common plane, and the first and second pluralities of grooves overlap and intersect when mapped on a common plane.

30. The bone fixation plate as recited in claim 28, wherein the second body defines a locking hole extending through the first and second arms, and the first body defines an alignment aperture in alignment with the locking hole, such that a fastener can engage the first and second arms so as to retain the first and second arms against the insert portion.

31. The bone fixation plate as recited in claim 28, wherein the first body is initially translatable within the channel along both an inferior-superior direction and a lateral direction.

* * * * *